United States Patent
Akimoto et al.

(10) Patent No.: US 9,538,907 B2
(45) Date of Patent: Jan. 10, 2017

(54) ENDOSCOPE SYSTEM AND ACTUATION METHOD FOR DISPLAYING AN ORGAN MODEL IMAGE PASTED WITH AN ENDOSCOPIC IMAGE

(71) Applicant: OLYMPUS CORPORATION, Tokyo (JP)

(72) Inventors: Syunya Akimoto, Kawasaki (JP); Jun Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/858,074

(22) Filed: Sep. 18, 2015

(65) Prior Publication Data

US 2016/0000307 A1 Jan. 7, 2016

Related U.S. Application Data

(63) Continuation of application No. PCT/JP2014/060141, filed on Apr. 8, 2014.

Foreign Application Priority Data

Apr. 12, 2013 (JP) ................................ 2013-084301

(51) Int. Cl.
*A61B 1/04* (2006.01)
*A61B 1/045* (2006.01)
(Continued)

(52) U.S. Cl.
CPC ............ *A61B 1/045* (2013.01); *A61B 1/0002* (2013.01); *A61B 1/00006* (2013.01);
(Continued)

(58) Field of Classification Search
CPC .............. A61B 1/00009; A61B 1/0005; A61B 1/00181; A61B 1/307; A61B 1/00183; A61B 5/7425; G06T 11/60; G06T 2207/10068; G06T 7/0046
See application file for complete search history.

(56) References Cited

U.S. PATENT DOCUMENTS

2004/0249247 A1* 12/2004 Iddan .................. A61B 1/0005
600/170
2007/0060792 A1* 3/2007 Draxinger .......... A61B 1/00009
600/117
(Continued)

FOREIGN PATENT DOCUMENTS

EP 2335551 A1 6/2011
EP 2036049 B1 4/2012
(Continued)

OTHER PUBLICATIONS

International Search Report dated Jul. 1, 2014 issued in PCT/JP2014/060141.
(Continued)

*Primary Examiner* — John P Leubecker
(74) *Attorney, Agent, or Firm* — Scully, Scott, Murphy & Presser, P.C.

(57) ABSTRACT

An endoscope system includes an image pickup device that is inserted into a subject and picks up an image inside the subject and a memory that records an intra-subject image acquired by the image pickup device and position information of the image pickup device in association with each other. The endoscope system includes an image generating section that applies, to the intra-subject image, when it is determined that a release signal is generated as a predetermined trigger signal, predetermined processing for distinguishably displaying the intra-subject image at a time when the release signal is generated and generates an image
(Continued)

obtained by pasting the intra-subject image onto a model image of a predetermined organ.

17 Claims, 18 Drawing Sheets

(51) Int. Cl.
*A61B 1/00* (2006.01)
*A61B 1/06* (2006.01)
*A61B 1/307* (2006.01)

(52) U.S. Cl.
CPC ...... *A61B 1/00009* (2013.01); *A61B 1/00039* (2013.01); *A61B 1/00055* (2013.01); *A61B 1/00096* (2013.01); *A61B 1/00147* (2013.01); *A61B 1/04* (2013.01); *A61B 1/06* (2013.01); *A61B 1/307* (2013.01)

(56) References Cited

U.S. PATENT DOCUMENTS

| | | | |
|---|---|---|---|
| 2007/0149846 A1* | 6/2007 | Chen | A61B 1/00009 600/117 |
| 2007/0161853 A1 | 7/2007 | Yagi et al. | |
| 2007/0268287 A1 | 11/2007 | Magnin et al. | |
| 2009/0259102 A1* | 10/2009 | Koninckx | A61B 1/00181 600/111 |
| 2010/0097454 A1 | 4/2010 | Kubo et al. | |
| 2011/0242301 A1* | 10/2011 | Morita | A61B 1/00009 348/65 |
| 2012/0154562 A1* | 6/2012 | Munzenmayer | G06K 9/32 348/65 |
| 2012/0289825 A1* | 11/2012 | Rai | A61B 6/463 600/425 |
| 2012/0319006 A1 | 12/2012 | Shida | |
| 2013/0158352 A1 | 6/2013 | Imaizumi | |
| 2014/0296644 A1* | 10/2014 | Zilberstein | A61B 1/06 600/178 |
| 2015/0216403 A1* | 8/2015 | Whitmore, III | A61B 1/307 600/103 |
| 2015/0221116 A1* | 8/2015 | Wu | A61B 1/00009 382/128 |

FOREIGN PATENT DOCUMENTS

| | | |
|---|---|---|
| EP | 2543308 A1 | 1/2013 |
| EP | 2649929 A1 | 10/2013 |
| EP | 2 868 256 A1 | 5/2015 |
| JP | H11-104072 A | 4/1999 |
| JP | 2007-236700 A | 9/2007 |
| JP | 2010-508047 A | 3/2010 |
| JP | 2010-099171 A | 5/2010 |
| JP | 2010-240000 A | 10/2010 |
| JP | 2011-177419 A | 9/2011 |
| JP | 5274724 B2 | 8/2013 |
| WO | WO 2007/139697 A2 | 12/2007 |
| WO | WO 2011/108354 A1 | 9/2011 |
| WO | WO 2012/157338 A1 | 11/2012 |

OTHER PUBLICATIONS

Japanese Office Action dated Jan. 13, 2015 issued in JP-2014-550583.
Nainggolan, Tua Namora, "Sotaikan Yuketsu Shokogun ni Okeru Taiban Hyomen no Mapping System no Kaihatsu", The University of Tokyo, Mar. 22, 2007, retrieved from the Internet on Jun. 16, 2014, URL: http://repository.dl.itc.u-tokyo.ac.jp/dspace/bitstream/2261/20154/1/K-00928-a.pdf, with English Abstract.
Arai, Kohei, "3D image reconstruction acquired with arrayed optical fiber", Saga University, Dec. 1, 2007, retrieved from the Internet on Jun. 16, 2014, URL: http://portal.dl.saga-u.ac.jp/bitstream/123456789/55466/1/ZR00006124.pdf, with English Abstract.
Extended Supplementary European Search Report dated Oct. 7, 2016 in European Patent Application No. 14 78 2663.0.

* cited by examiner

ENDOSCOPE SYSTEM AND ACTUATION METHOD FOR DISPLAYING AN ORGAN MODEL IMAGE PASTED WITH AN ENDOSCOPIC IMAGE

CROSS REFERENCE TO RELATED APPLICATION

This application is a continuation application of PCT/JP2014/060141 filed on Apr. 8, 2014 and claims benefit of Japanese Application No. 2013-084301 filed in Japan on Apr. 12, 2013, the entire contents of which are incorporated herein by this reference.

BACKGROUND OF THE INVENTION

1. Field of the Invention

The present invention relates to an endoscope system and an actuation method for the endoscope system and, more particularly, to an endoscope system that displays an organ model image pasted with an endoscopic image and an actuation method for the endoscope system.

2. Description of the Related Art

Conventionally, endoscope systems are widely used in a medical field and an industrial field. For example, in the endoscope system in the medical field, a surgeon inserts an insertion section of an endoscope into a subject. An endoscopic image obtained through an observation window provided at a distal end portion of the insertion section is displayed on a display apparatus. The surgeon can perform an endoscopic examination viewing the displayed endoscopic image. Further, the endoscope system can also record the endoscopic image. For example, a doctor can use a recorded endoscopic image of a lesion part as a part of a clinical record.

In recent years, a capsule-type endoscope system has also been put to practical use. When a patient swallows a capsule-type endoscope, the capsule-type endoscope picks up images inside a body and records the images inside the body while moving in the body.

In the case of the capsule endoscope, since an enormous number of images are acquired, there have been proposed a technique for extracting only an image of a site to be observed such as a lesion part out of an acquired large number of images and a technique for generating an image for diagnosis using images with high priority levels on the basis of feature parameters when a plurality of images are pasted onto a 3D model as disclosed in Japanese Patent Application Laid-Open Publication No. 2010-240000.

Furthermore, Japanese Patent Application Laid-Open Publication No. 2007-236700 proposes a technique for developing omnidirectional images obtained by a capsule-type endoscope to create developed images, extracting blood vessel patterns and structure patterns in the developed images, joining the developed images on the basis of a result of the extraction, and displaying the developed images over a contour diagram of an organ.

Incidentally, in order to observe a state of a lesion part found in a last endoscopic examination, the endoscopic examination is performed again or the lesion part found in the last endoscopic examination is treated using an endoscope.

Therefore, a doctor writes, in a clinical record, a position of the lesion part found in the examination in an examination target organ. For example, when the examination target organ is a bladder, the position of the lesion part is designated by marking on a bladder development view (schema) drawn in the clinical record.

SUMMARY OF THE INVENTION

According to an aspect of the present invention, it is possible to provide an endoscope system including: an insertion section that is inserted into a subject; an objective optical window that is provided on a distal end side of the insertion section and receives light from the subject; an image pickup section that picks up an image inside the subject from the light made incident from the objective optical window; a position-information acquiring section that acquires position information of the objective optical window; a recording section that records an intra-subject image acquired by the image pickup section and the position information acquired by the position-information acquiring section in association with each other; an associating section that associates the position information recorded in the recording section with a model image of a predetermined organ in the subject; an image generating section that generates, as a pasted image, an image obtained by pasting the intra-subject image onto the model image of the predetermined organ associated by the associating section; a determining section that determines whether a predetermined trigger signal concerning the image pickup in the image pickup section is generated or a predetermined feature value of the intra-subject image acquired by the image pickup section satisfies a predetermined condition; and a control section that applies processing for pasting the intra-subject image, concerning which the predetermined trigger signal is determined as being generated or the predetermined feature value of which is determined as satisfying the predetermined condition by the determining section, closer to a front surface than other intra-subject images on the pasted image and applies image processing to the intra-subject image pasted onto the front surface to be distinguishable from the other intra-subject images.

According to an aspect of the present invention, it is possible to provide an actuation method for an endoscope system including an image pickup section that picks up an image inside a subject from light made incident from an objective optical window provided on a distal end side of an insertion section inserted into the subject, a position-information acquiring section that acquires position information of the objective optical window, a recording section that records an intra-subject image acquired by the image pickup section and the position information acquired by the position-information acquiring section in association with each other, an associating section, an image generating section, a determining section, and a control section, the actuation method comprising: the associating section associating the position information recorded in the recording section with a model image of a predetermined organ in the subject; the image generating section generating, as an intra-subject image pasted image, an image obtained by pasting the intra-subject image onto the model image of the predetermined organ associated by the associating section; the determining section determining whether a predetermined trigger signal concerning the image pickup in the image pickup section is generated or a predetermined feature value of the intra-subject image acquired by the image pickup section satisfies a predetermined condition; and the control section applying processing for pasting the intra-subject image, concerning which the predetermined trigger signal is determined as being generated or the predetermined feature value of which is determined as satisfying the predetermined condition by the determining section, closer to a front surface than other intra-subject images on the pasted image and applies image processing to the intra-subject image pasted onto the front surface to be distinguishable from the other intra-subject images.

DETAILED DESCRIPTION OF THE PREFERRED EMBODIMENT

Embodiments of the present invention are explained below with reference to the drawings. In the following explanation, in the embodiments of the present invention, acquisition of an endoscopic image inside a bladder is explained as an example.

First Embodiment

Configuration

Figure 1:
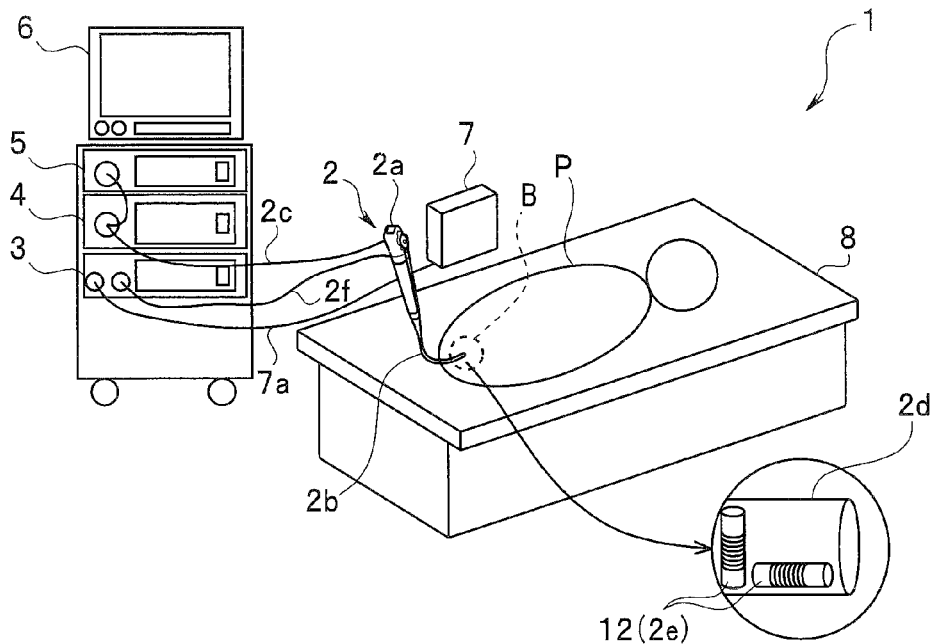
FIG. 1 is a configuration diagram showing a configuration of an endoscope system according to a first embodiment of the present invention.
Figure 2:
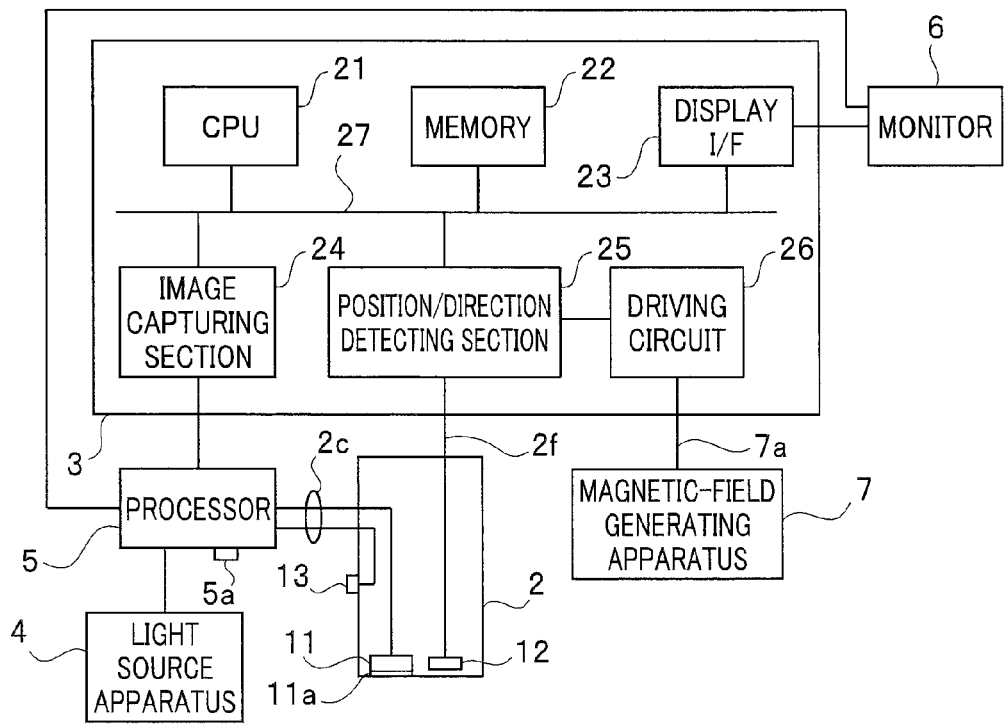
FIG. 2 is a block diagram showing a configuration of an endoscope system 1 according to the first embodiment of the present invention.

FIG. 1 is a configuration diagram showing a configuration of an endoscope system according to the present embodiment. FIG. 2 is a block diagram showing a configuration of an endoscope system 1. The endoscope system 1 includes an endoscope 2, a recording apparatus 3, a light source apparatus 4, a processor 5, a monitor 6, and a magnetic-field generating apparatus 7. The endoscope system 1 has two observation modes, i.e., a normal light observation and a special light observation. A doctor, who is an examiner, performs an endoscopic examination of a bladder B of a patient P lying on his or her back on a bed 8.

The endoscope 2 includes an operation section 2a, an insertion section 2b that has flexibility and is inserted into a subject, and a universal cable 2c. The endoscope 2 is an endoscope for a bladder examination.

Further, although not shown in the figure, a light guide is inserted through the universal cable 2c. The endoscope 2 is configured to emit illumination light, which is received from a light source apparatus 4, from a distal end portion 2d of the insertion section 2b through the light guide.

As shown in FIG. 2, an image pickup device 11 is provided at the distal end portion 2d of the insertion section 2b. An image of a part in the bladder B illuminated by the illumination light of the light source apparatus 4 is picked up by the image pickup device 11 via an objective optical window 11a. The objective optical window 11a is provided on a distal end side of the insertion section 2b and receives light from the subject. That is, the image pickup device 11 configures an image pickup section that is inserted into the subject and picks up an inside of the subject from light made incident from the objective optical window 11a. An image pickup signal obtained by the image pickup device 11 is supplied to the processor 5 via a signal line in the universal cable 2c. The image pickup signal is subjected to image processing in the processor 5.

The processor 5 includes a changeover switch 5a for changing over the observation modes. The processor 5 generates an endoscopic image corresponding to the observation mode designated by the changeover switch 5a.

The generated endoscopic image is outputted from the processor 5 to the monitor 6. A live endoscopic image is displayed on the monitor 6. The doctor who performs examination (hereinafter referred to as examiner) can insert the distal end portion 2d of the insertion section 2b from a urethra of the patient P and observe an inside of the bladder B (indicated by a dotted line in FIG. 1) of the patient P.

Further, a magnetic sensor 12 is disposed at the distal end portion 2d of the insertion section 2b. More specifically, the magnetic sensor 12 including two coils 2e is provided in a vicinity of the objective optical window 11a of the distal end portion 2d. Therefore, the magnetic sensor 12 is a six-axis sensor. A signal line 2f of the magnetic sensor 12 extends from the endoscope 2 and is connected to the recording apparatus 3.

Note that the magnetic sensor 12 may be a five-axis sensor.

The magnetic-field generating apparatus 7 generates a predetermined magnetic field. The magnetic sensor 12 detects the magnetic field generated by the magnetic-field generating apparatus 7. A detection signal of the magnetic field is supplied from the endoscope 2 to the recording apparatus 3 via the signal line 2f.

A release button 13 is provided in the operation section 2a of the endoscope 2. The release button 13 is a button to be pressed when the examiner records an endoscopic image. When the release button 13 is pressed, a release button operation signal is inputted to the processor 5. The processor 5 generates a release signal and supplies the release signal to the recording apparatus 3. The endoscopic image at a time when the release button 13 is pressed is recorded in a memory 22 explained below of the recording apparatus 3.

The recording apparatus 3 includes a central processing unit (hereinafter referred to as CPU) 21, a memory 22, a display interface (hereinafter abbreviated as display I/F) 23, an image capturing section 24, a position/direction detecting section 25, and a driving circuit 26. The CPU 21, the memory 22, the display interface (hereinafter abbreviated as display I/F) 23, the image capturing section 24, the position/direction detecting section 25, and the driving circuit 26 are connected to one another via a bus 27.

The CPU 21 is a control section that controls processing of the sections in the recording apparatus 3.

The memory 22 is a storing section including a ROM, a RAM, and a flash memory. Various processing programs and various data to be executed by the CPU 21 are stored in the memory 22. Further, as explained below, endoscopic image information, information concerning a position and a direction, and the like are also stored in the memory 22.

In the memory 22, data of a model image of an organ explained below (hereinafter referred to as organ model image) is also stored. As explained below, an endoscopic image is pasted onto the organ model image. As explained below in detail, the CPU 21 performs, on the basis of position/direction information of the distal end portion 2d at a time when the endoscopic image is picked up, processing for pasting the endoscopic image on the model image stored in advance and stores the organ model image pasted with the endoscopic image in the memory 22. The organ model image stored in the memory 22 is used as a part of a clinical record.

The organ model image stored in the memory 22 is outputted via the display I/F 23 and displayed on the screen of the monitor 6.

Further, the processor 5 is also connected to the monitor 6. The monitor 6 has a PinP (picture in picture) function and can display, together with the organ model image pasted with the endoscopic image by the CPU 21, a live endoscopic image obtained by picking up an image with the image pickup device 11 of the endoscope 2.

The image capturing section 24 is a processing section that captures, at a fixed cycle, an image obtained in the processor 5. For example, the image capturing section 24 acquires, from the processor 5, thirty endoscopic images per second, which is the same as a frame rate. The image capturing section 24 also receives a release signal from the processor 5. Note that, although the image capturing section 24 captures thirty endoscopic images per second, the image capturing section 24 may acquire endoscopic images at a longer cycle, for example, three endoscopic images per second, which is different from the frame rate.

The position/direction detecting section 25 controls the driving circuit 26, which drives the magnetic-field generating apparatus 7, causes the magnetic-field generating apparatus 7 to generate a predetermined magnetic field, detects the magnetic field with the magnetic sensor 12, and generates, on a real-time basis, data of a position coordinate (x, y, z) and an orientation (i.e., an Eulerian angle (ϕ, θ, φ)), that is, position/direction information of the objective optical window 11a from a detection signal of the detected magnetic field. That is, the position/direction detecting section 25 configures a position/information acquiring section that acquires position information and direction information from the magnetic sensor 12 and acquires position information of the objective optical window 11a.

The CPU 21 stores the image captured by the image capturing section 24 and information concerning a position and a direction of the distal end portion 2d calculated from the position/direction information detected by the position/direction detecting section 25 in the memory 22 in association with each other.

Further, the CPU 21 has a stereo measurement function and has a function of measuring, from two frame images obtained by performing image pickup, distances to respective parts of a target region in the frame images. More specifically, the CPU 21 can acquire image pickup position information of the objective optical window 11a on the basis of position/direction information from the position/direction detecting section 25 at a time when the two frame images are picked up and calculate, from a parallax at the time when the two frame images are picked up, distances from the image pickup device 11 to respective parts in the frame images. A program for the stereo measurement function is stored in the memory 22. The CPU 21 can perform stereo measurement by reading out and executing the program.

The light source apparatus 4 is a light source apparatus capable of emitting normal light for a normal light observation mode and special light for a special light observation mode. The light source apparatus 4 emits one of the normal light and the special light as illumination light according to a state of the changeover switch 5a for changing over the observation modes provided in the processor 5.

The special light observation mode is a narrowband observation mode. Note that the special light observation mode may be an infrared-ray observation mode or a florescent observation mode. Therefore, the endoscope system 1 has two observation modes, i.e., the normal light observation mode and the special light observation mode. The light source apparatus 4 emits illumination light of the normal light when the changeover switch 5a is in the normal light observation mode and emits illumination light of narrow-band light having a predetermined wavelength when the changeover switch 5a is in the special light observation mode. That is, the light source apparatus 4 configures an illuminating section that irradiates white light or special light having a predetermined wavelength band on the subject while being capable of changing over the white light and the special light.

Therefore, the processor 5 generates, during the normal light observation mode, a normal light observation image of the subject obtained by irradiating the white light on the subject and generates, during the special light observation mode, a special light observation image of the subject obtained by irradiating the special light (the narrowband light) on the subject.

Note that, a narrowband observation image, which is the special light observation image, can also be obtained by applying spectral estimation processing to respective images of RGB obtained by the irradiation of the normal light. Therefore, during the narrowband observation mode, the processor 5 may generate the narrowband observation image through spectral estimation.

(Processing for Pasting an Endoscopic Image to an Organ Model Image)

Figure 3:
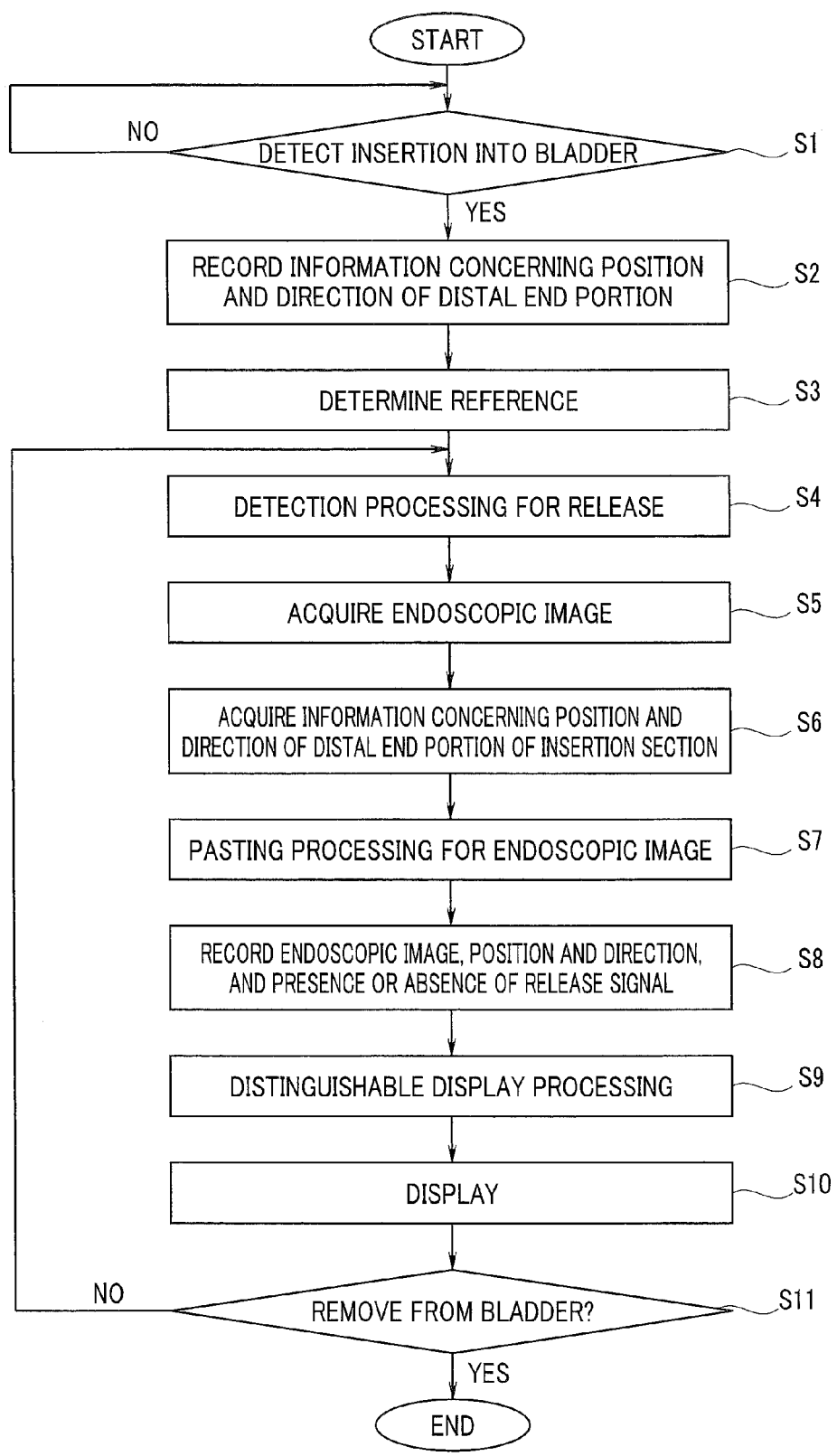
FIG. 3 is a flowchart for explaining an example of a flow of processing for pasting an endoscopic image to a bladder model image during observation inside a bladder according to the first embodiment of the present invention.

FIG. 3 is a flowchart for explaining an example of a flow of processing for pasting an endoscopic image to a bladder model image. The processing shown in FIG. 3 is executed from time when the CPU 21 reads out and executes a predetermined program stored in the memory 22, whereby the examiner inserts the distal end portion 2d of the insertion section 2b into the urethra.

The CPU 21 determines whether the insertion of the distal end portion 2d into the bladder B is detected (S1). The distal end portion 2d of the insertion section 2b is inserted into the urethra and enters inside the bladder B through the urethra. The detection of the insertion of the distal end portion 2d into the bladder B is performed on the basis of an amount of change of luminance of the endoscopic image acquired by the image capturing section 24 (average luminance of the entire endoscopic image or average luminance of a predetermined part of a region of the endoscopic image). That is, the CPU 21 performs the determination in S1 making use of a change in the luminance of the endoscopic image that occurs when the distal end portion 2d enters inside the bladder B from the urethra. When a luminance value of the endoscopic image changes from a high state to a low state, the CPU 21 determines that the distal end portion 2d enters inside the bladder B.

Note that, the detection of the insertion of the distal end portion 2d into the bladder B is performed on the basis of the luminance of the endoscopic image. However, the detection may be performed on the basis of an amount of change in a tint of the endoscopic image or an amount of change in texture. For example, the change in the tint is a change in a color from red to other colors. The change in texture is a change from a state of an image in which patterns of blood vessels and the like cannot be recognized to a state in which the patterns of the blood vessels and the like can be recognized.

When the insertion into the bladder B is detected (S1: YES), the CPU 21 records, as reference information of a position and a direction of the distal end portion 2d (more specifically, the objective optical window 11a), position/direction information of the position/direction detecting section 25 at a time when the insertion is detected (S2).

The CPU 21 performs reference determination for setting the position and the direction of the distal end portion 2d recorded in S2 respectively as a reference position and a reference direction of a three-dimensional bladder model (hereinafter referred to as 3D bladder model) M1 (S3). According to the processing in S3, the CPU 21 can perform conversion from a first coordinate system $(X_0Y_0Z_0)$ based on the magnetic-field generating apparatus 7 outside a body into a coordinate system $(X_1Y_1Z_1)$ based on an entrance (a neck) of the bladder B and conversion from the coordinate system $(X_1Y_1Z_1)$ into a coordinate system $(X_2Y_2Z_2)$ based on a center of the bladder model M1. The conversion of the coordinate systems is explained below.

Therefore, the processing in S1 to S3 configures an aligning section that aligns, on the basis of an amount of change in intra-subject image information inside the patient P, who is a subject, a position in a coordinate system of a predetermined organ model image inside the patient P from position information of the objective optical window 11a.

An examination of the bladder B is performed in a state in which the patient lies on his or her back and a state in which the bladder B is filled with predetermined liquid (e.g., saline). For example, if the patient is an adult, there is no large difference in a size of the bladder B if any. The bladder B can be modeled in a spherical shape having a substantially same size.

Figure 4:
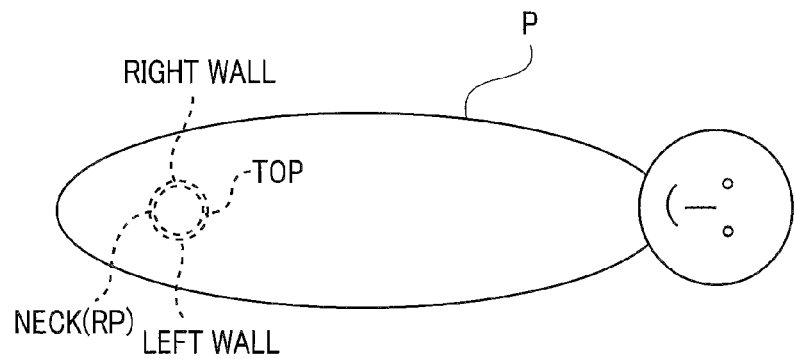
FIG. 4 is a diagram showing a position of a bladder of a schematic patient for explaining names of respective parts of the bladder according to the first embodiment of the present invention.
Figure 5:
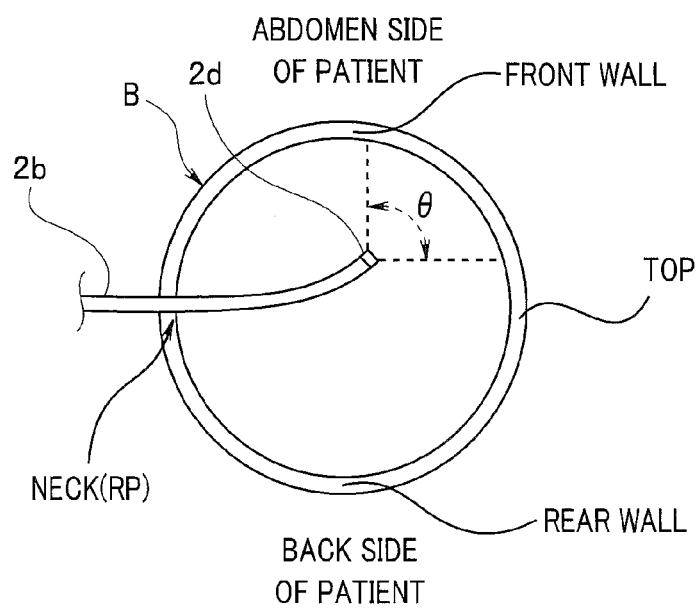
FIG. 5 is a diagram showing a schematic bladder for explaining names of respective parts of the bladder according to the first embodiment of the present invention.

FIG. 4 is a diagram showing a position of a bladder of a schematic patient for explaining names of respective parts of the bladder. FIG. 4 is a view from a direction opposed to a front of the patient P. FIG. 5 is a diagram showing a schematic bladder for explaining names of respective parts of the bladder. FIG. 5 is a diagram of the bladder viewed from a left side of the patient P.

The bladder B is divided into a plurality of regions including a neck RP, which is an opening portion of a urethra and is an entrance to the bladder B, a top opposed to the neck RP, a front wall on an abdomen side, a rear wall on a back side, a right wall on a right side viewed from the patient P, and a left wall on a left side viewed from the patient P. The examination of the bladder B is performed in a state in which the patient P lies on his or her back and the state in which the bladder B is filled with the predetermined liquid. Therefore, it is difficult for the examiner to understand a position and a direction of the entire real bladder B.

Referring back to FIG. 3, when the insertion of the distal end portion 2d into the bladder B is not detected (S1: NO), the processing repeats the processing in S1. When the insertion of the distal end portion 2d into the bladder B is detected (S1: YES), the distal end portion 2d is present in the neck RP of the bladder B. The magnetic sensor 12 generates the position/direction information of six axes (i.e., the position coordinate (x, y, z) and the orientation (the Eulerian angle ($\phi$, $\theta$, $\psi$)). Therefore, the recording apparatus 3 records a position and a direction at a time when the insertion of the distal end portion 2d into the bladder B is detected. By setting the recorded position and the recorded direction as a reference position and a reference direction of the objective optical window 11a with respect to the 3D bladder model M1, it is possible to align the reference position and the reference direction and the position and the direction of the neck RP in the 3D bladder model M1.

As shown in FIG. 5, the image pickup device 11 provided at the distal end portion 2d of the insertion section 2b picks up an endoscopic image at an angular field of view $\theta$ inside the bladder B.

Figure 6:
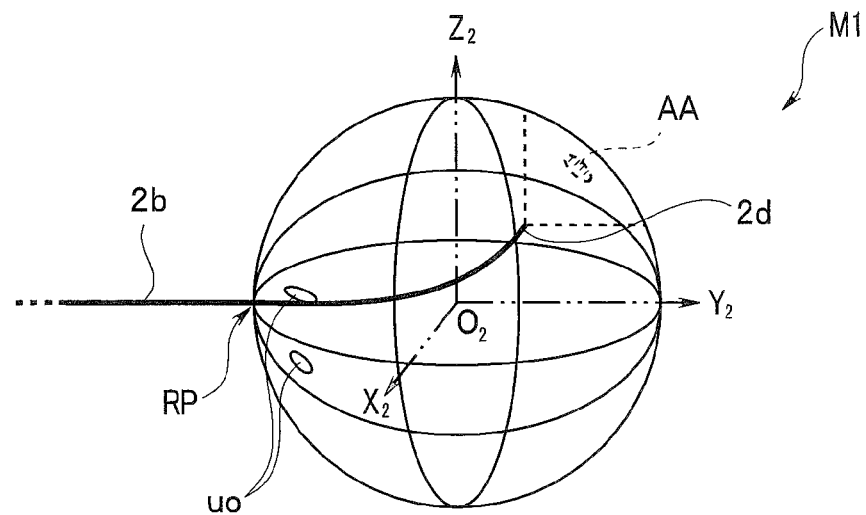
FIG. 6 is a diagram showing a 3D bladder model M1 according to the first embodiment of the present invention.

FIG. 6 is a diagram showing the 3D bladder model M1. The 3D bladder model M1 is a substantially spherical shape and is formed in a three-dimensional coordinate system $X_2Y_2Z_2$. The coordinate system $X_2Y_2Z_2$ is a coordinate system converted from the coordinate system $X_1Y_1Z_1$. Note that, in FIG. 6, in order to show the neck RP, which is the entrance of the insertion section 2b inside the bladder B, a figure of the insertion section 2b is also shown.

The 3D bladder model M1 is formed with an $X_2$ axis set in an axis extending in a direction from a right wall to a left wall passing a center O of a sphere, a $Y_2$ axis set in an axis extending in a direction from a neck to a top passing the center O of the sphere, and a $Z_2$ axis set in an axis in a direction from a rear wall to a front wall passing the center O of the sphere.

Figure 7:
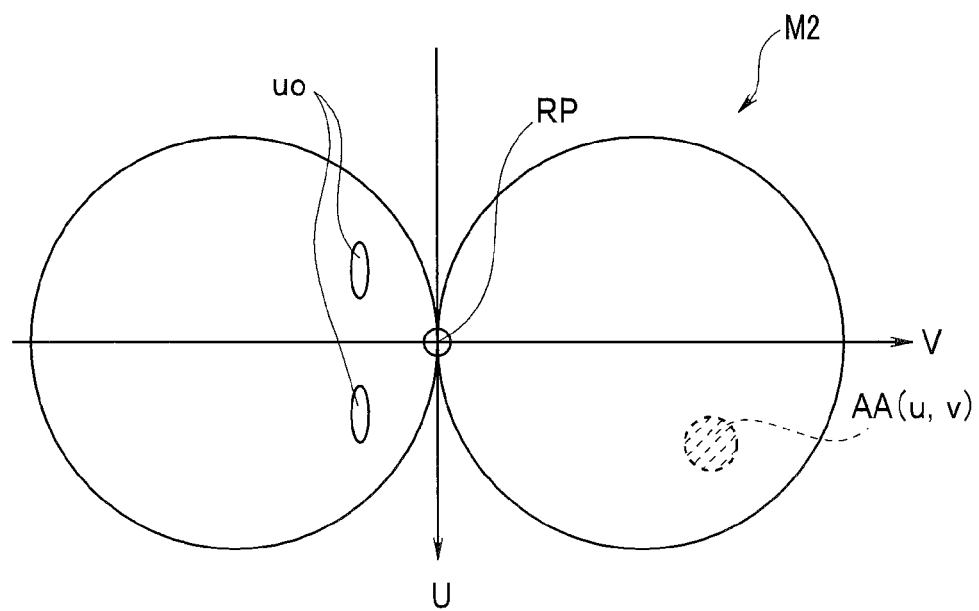
FIG. 7 is a diagram showing a two-dimensional model M2 of a bladder B according to the first embodiment of the present invention.
Figure 8:
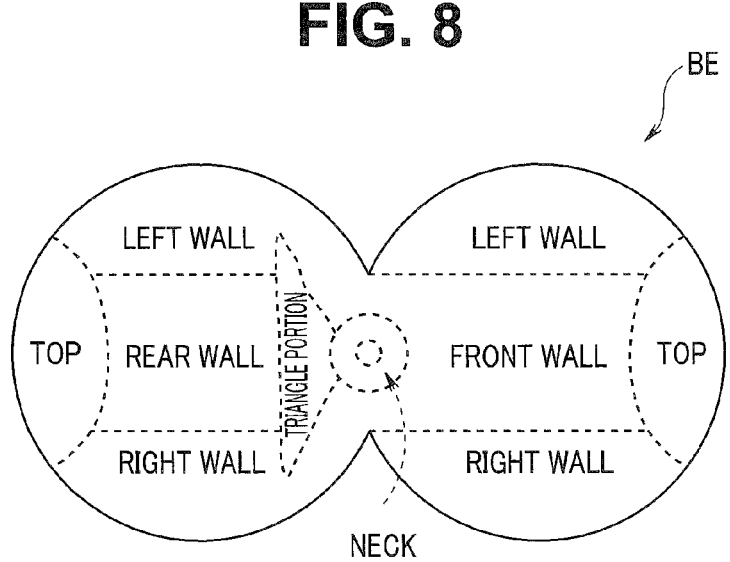
FIG. 8 is a diagram showing a bladder development view BE.

FIG. 7 is a diagram showing a two-dimensional model (hereinafter referred to as 2D bladder model) M2 of the bladder B. The 2D bladder model M2 has a shape including two circular shapes and is formed inside a two-dimensional coordinate system UV. The 2D bladder model M2 has a shape substantially the same as a shape of a bladder development view (schema) BE shown in FIG. 8. FIG. 8 is a diagram showing the bladder development view BE. The bladder development view BE is a diagram showing positions of respective parts inside the bladder B. As shown in FIG. 8, the respective parts inside the bladder B correspond to respective predetermined regions on the bladder development view BE.

Two urethra orifices of the bladder B are present in positions indicated by uo in FIG. 6 and FIG. 7. For example, when a lesion part AA is present inside the bladder B in a position indicated by a dotted line in FIG. 6, a position of the lesion part AA shown in FIG. 6 corresponds to a position indicated by a dotted line in FIG. 7.

Referring back to FIG. 3 again, information concerning the position and the direction of the distal end portion 2d at the time when the insertion of the distal end portion 2d into the bladder B is detected is recorded as reference information in S2. A reference of the 3D bladder model M1 and a reference of the 2D bladder model M2 are derived from the position and the direction designated by the reference information.

Subsequently, the CPU 21 performs processing for detecting release (S4). The processing for detecting release is processing for detecting whether the release button 13 of the operation section 2a of the endoscope 2 is pressed. When the release button 13 is pressed, a release signal is inputted to the image capturing section 24 via the processor 5. The release signal is a trigger signal for recording an intra-subject image acquired by the image pickup device 11, which is an image pickup section. The CPU 21 can detect, by monitoring a rising edge (or a falling edge) of the release signal inputted to the image capturing section 24, whether the release button 13 is pressed.

Therefore, the processing in S4 configures a determining section that determines whether the release signal serving as a predetermined trigger signal concerning the image pickup in the image pickup device 11 is generated.

The CPU 21 acquires the endoscopic image from the image capturing section 24 (S5). As explained above, the image capturing section 24 acquires the endoscopic image from the processor 5 at every 1/30 second, which is the same as a frame rate.

The CPU 21 acquires the information concerning the position and the direction of the distal end portion 2d of the insertion section 2b (S6). The CPU 21 can acquire the information concerning the position and the direction of the distal end portion 2d by reading out the position/direction information from the position/direction detecting section 25.

In S6, the CPU 21 converts, on the basis of the reference information determined in S3, position/direction information in the coordinate system ($X_0Y_0Z_0$) into position/direction information in the three-dimensional coordinate system ($X_2Y_2Z_2$). After the position information of the objective optical window 11a and the coordinate system of the bladder model image, which is the predetermined bladder model image, are aligned in S1 to S3, in S6, association of the position and the direction of the distal end portion 2d (i.e., a position and a direction of the objective optical window 11a) acquired by the position/direction detecting section 25 and the position and the direction in the coordinate system of the bladder model image is performed. That is, the processing in S6 configures an associating section that associates the position information recorded in the memory 22, which is a storing section in S8, with a model image of a predetermined organ in the subject.

The CPU 21 performs processing for pasting the endoscopic image (S7). The processing for pasting the endoscopic image is processing for pasting, on the basis of the position/direction information converted into the three-dimensional coordinate system ($X_2Y_2Z_2$) acquired in S6, an endoscopic image pasted onto an inner surface of the 3D bladder model M1, which is a sphere, onto a diagram of the 2D model M2 (hereinafter referred to as 2D model image).

That is, the processing in S7 configures a part of an image generating section that generates, as an intra-subject pasted image, an image obtained by pasting an intra-subject image on a model image of a predetermined organ in which the position of the objective optical window 11a and the position in the coordinate system of the 3D model image are associated by S1 to S3 that configure the aligning section. The pasting processing in S7 is performed by pasting an endoscopic image projected on the sphere inner surface of the 3D bladder model M1 specified by the three-dimensional coordinate system $(X_2Y_2Z_2)$ onto a position on an image of the 2D bladder model M2 in the two-dimensional coordinate system (U, V).

The position and the direction of the endoscopic image pasted onto the image of the 2D bladder model M2 are determined as explained above. A size of the endoscopic image to be pasted is changed, for example, according to distances to the distal end portion 2d and an image pickup part of the bladder B.

The reference information of the position and the direction determined in S3 is a position and a direction in the three-dimensional coordinate system $(X_0Y_0Z_0)$ determined on the basis of the magnetic-field generating apparatus 7 outside the body. The position and the direction in the pasting processing in S7 are a position and a direction in the two-dimensional coordinate system (U, V) based on the neck RP of the 2D bladder model M2.

Therefore, the CPU 21 derives position/direction information of the distal end portion 2d in a two-dimensional coordinate system from the reference information obtained in S3 and calculates, on the basis of the derived position/direction information, a position and a tilt for projecting and pasting the endoscopic image onto the 2D model image.

When the endoscopic image is already pasted to a position where the endoscopic image is to be pasted, the pasting of the endoscopic image in S7 is performed to superimpose and paste an image acquired later onto the endoscopic image acquired and pasted earlier.

The CPU 21 records, in the memory 22, respective kinds of information of the pasted endoscopic image, the position and the direction on the 2D model image, and presence or absence of the release signal (S8). That is, the processing in S8 configures a recording section that records the endoscopic image, which is the intra-subject image, acquired by the image pickup device 11 and the position information and the direction information acquired by the position/direction detecting section 25 in association with each other.

Subsequently, the CPU 21 executes distinguishable display processing (S9). The distinguishable display processing is processing for, when there are a plurality of endoscopic images to be pasted onto the 2D model image and the endoscopic images are pasted to entirely or partly overlap one another, arranging endoscopic images with a release signal in a forefront such that the endoscopic images are not prevented from being displayed by the other endoscopic images and can be recognized to be distinguished from the other endoscopic images. That is, intra-subject images at a time when the release button 13 of the endoscope 2 is pressed are pasted onto a forefront on a model image of a predetermined organ more preferentially than other intra-subject images. Further, for distinguishable display, predetermined frames 41 (see FIG. 10) are added to the endoscopic images at the time when the release button 13 is pressed to make it possible to distinguish at a glance the endoscopic images at the time when the release button 13 is pressed and the other endoscopic images.

Note that, when all or a part of the plurality of endoscopic images with the release signal overlap in S9, the processing is performed such that an image acquired later is superimposed on the endoscopic image acquired and pasted earlier and is pasted such that the image can be recognized to be distinguished from the endoscopic images acquired and pasted earlier.

Therefore, the processing in S9 is performed only for a pixel region where pixels of the already pasted other endoscopic images are present in pixel positions of the endoscopic image pasted in S7.

The CPU 21 displays the 2D model image subjected to the distinguishable display processing on the monitor 6 via the display I/F 23 (S10). At this point, the CPU 21 also generates a 3D model image and displays the 3D model image together with the 2D model image. The CPU 21 generates an image of the insertion section 2b on the basis of the position/direction information of the distal end portion 2d and superimposes the image on the 3D model image to thereby generate a 3D model image.

As explained above, the processing in S7 and S9 configures a display section that applies, to the intra-subject image, when it is determined in the determining section in S4 that the release signal serving as the predetermined trigger signal is generated, the predetermined processing in S9 for distinguishably displaying intra-subject images at a time when the predetermined trigger signal is generated and generates and displays an image obtained by pasting the intra-subject images onto the model image of the predetermined organ associated by the associating section in S6. The predetermined processing in S9 is processing for adding the frame images 41 to the intra-subject images at the time when the release signal serving as the predetermined trigger signal is generated. When the release signal, which is the predetermined trigger signal, is not generated in the determining section in S4, the display section does not perform the predetermined processing in S9 for distinguishably displaying the intra-subject images.

In S10, the CPU 21 estimates a shape of the insertion section on the basis of the information concerning the position and the direction of the distal end portion 2d acquired in S6 and generates an image of the insertion section 2b having the estimated shape. Therefore, the processing in S10 configures a shape estimating section that performs shape estimation for the insertion section 2b on the basis of the position information and the direction information of the distal end portion 2d acquired in S6 and position information and direction information of the neck RP. In S10, processing for superimposing an insertion section image, which is shape information estimated by the shape estimating section, on the 3D model image concerning the predetermined organ is executed.

The CPU 21 determines whether the distal end portion 2d of the insertion section 2b is removed from the bladder B (S11). The determination in S11 can be performed by determining whether a position coordinate of the distal end portion 2d moves from the neck of the bladder B into the urethra.

When the distal end portion 2d is not removed from the bladder B (S11: NO), the processing returns to S4. The CPU 21 repeats the processing in S4 to S11 until the distal end portion 2d is removed from the bladder B.

Figure 9:
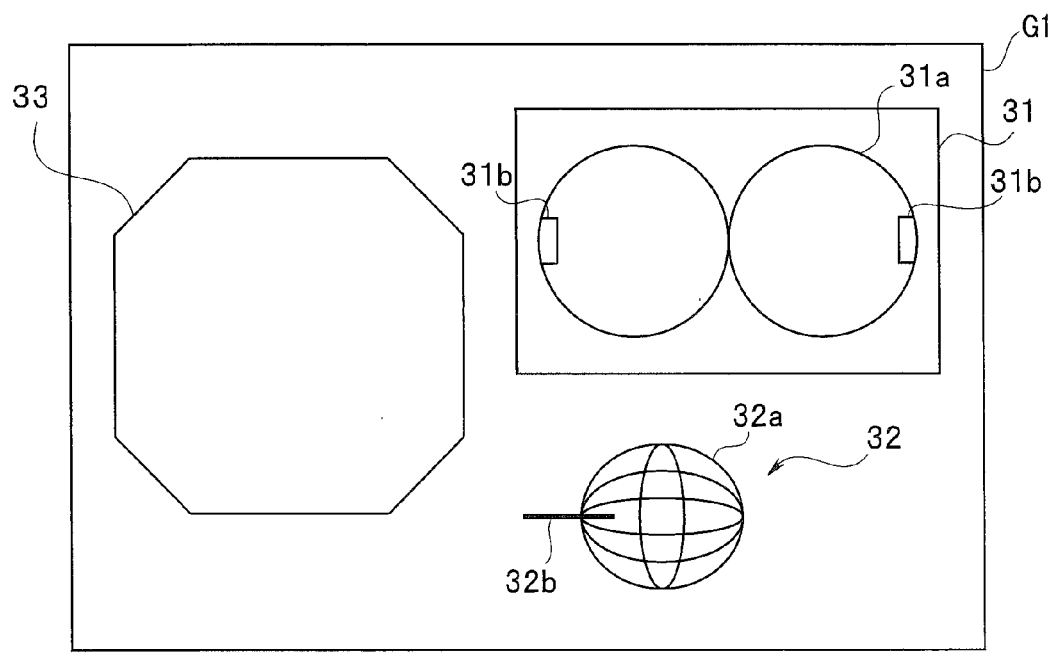
FIG. 9 is a diagram showing an example of a display screen during an endoscopic examination displayed on a screen of a monitor 6 according to the first embodiment of the present invention.

FIG. 9 is a diagram showing an example of a display screen during an endoscopic examination displayed on the screen of the monitor 6. As shown in FIG. 9, a screen G1 is a screen generated by the CPU 21 and includes a 2D-model-image display section 31, a 3D-model-image display section 32, and a live-image display section 33 that displays a live endoscopic image (hereinafter referred to as live image).

The 2D-model-image display section 31 is a region where the 2D model image corresponding to the 2D model shown in FIG. 7 is displayed. On the 2D-model-image display section 31, a 2D model image 31*a*, which is a 2D bladder development view, and an endoscopic image 31*b*, which is an intra-subject image pasted onto the 2D model image 31*a* by the processing in S7 and S9, are displayed.

The 3D-model-image display section 32 is a region where the 3D model image corresponding to the 3D model shown in FIG. 6 is displayed. On the 3D-model-image display section 32, a 3D model image 32*a* and an insertion section image 32*b* indicating a position and a direction of the distal end portion 2*d* of the insertion section 2*b* in the 3D model are displayed. As explained above, the CPU 21 generates the insertion section image 32*b* on the basis of present position/direction information of the distal end portion 2*d*.

The 2D-model-image display section 31 shown in FIG. 9 displays an image at a time when an endoscopic image picked up first when the distal end portion 2*d* enters inside the bladder B and faces a top direction is pasted onto the 2D model image 31*a*.

As explained above, the live intra-subject image acquired by the image pickup device 11 is displayed together with the model image. Further, the insertion shape of the insertion section 2*b* including the image pickup device 11 that picks up the live intra-subject image is also displayed together with the model image.

The live-image display section 33 is a region where an endoscopic image acquired by the monitor 6 from the processor 5 is directly displayed. The live-image display section 33 is included in the screen G1 by, for example, a PinP function of the monitor 6.

Note that the live endoscopic image is displayed on the monitor 6 using the PinP function of the monitor 6. However, the live image may be combined in the screen G1 by the CPU 21 of the recording apparatus 3 and outputted to the monitor 6.

Figure 10:
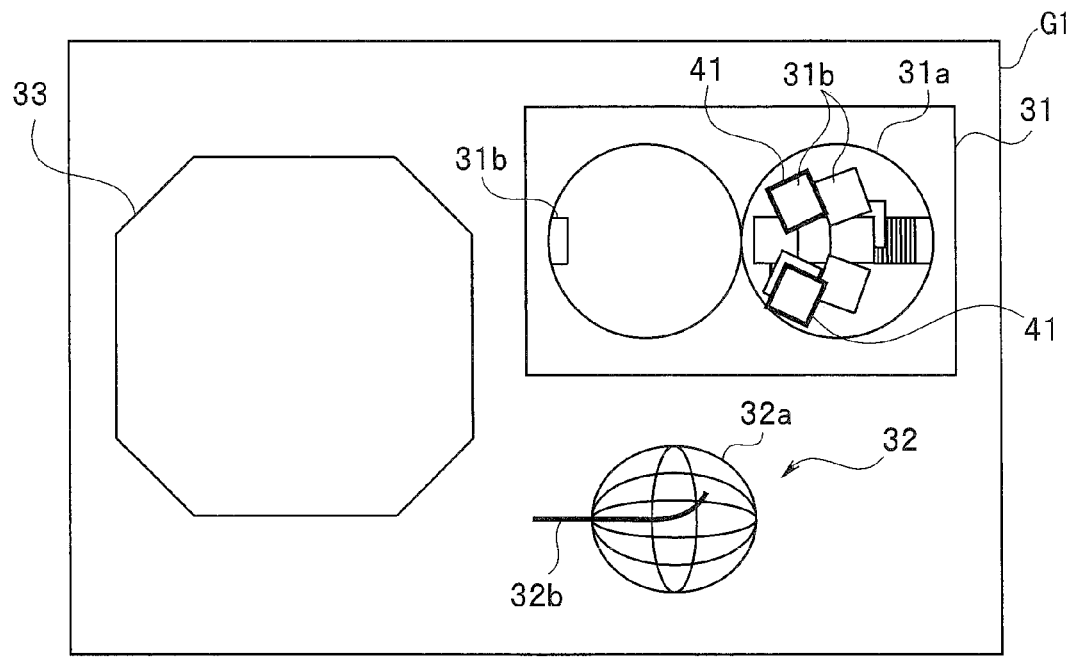
FIG. 10 is a diagram showing another example of the display screen displayed on the screen of the monitor 6 according to the first embodiment of the present invention.

FIG. 10 is a diagram showing another example of the display screen displayed on the screen of the monitor 6. The 2D-model-image display section 31 shown in FIG. 10 displays an image at a time when a plurality of endoscopic images 31*b* picked up when the distal end portion 2*d* moves and faces in various directions are pasted onto the 2D model image 31*a*.

On the 2D model image 31*a*, according to the distinguishable display processing in S9, the predetermined frame images 41 are added to endoscopic images at a time when the release button 13 is pressed. Since color tones of endoscopic images pasted onto the 2D model image 31*a* are similar, if the frame images 41 are absent, it is difficult to distinguish the endoscopic images at the time when the release button 13 is pressed. By adding the frame images 41, the endoscopic images at the time when the release button 13 is pressed are made conspicuous. The examiner can distinguish at a glance the endoscopic images at the time when the release button 13 is pressed and the other endoscopic images. Therefore, it is possible to easily find out a small lesion part or a lesion part with little color tone change.

The processing in S4 to S11 is repeated at a predetermined cycle (a cycle of ⅓₀ second), whereby the plurality of endoscopic images acquired in S5 are superimposed by the pasting processing in S7. As shown in FIG. 10, the plurality of endoscopic images 31*b* are included in the 2D-model-image display section 31. A region where the plurality of endoscopic images are pasted is a region observed by the examiner Therefore, the examiner can easily distinguish the region observed by the endoscope simply by glancing at the image shown in FIG. 10.

While the processing in S4 to S11 is repeated, the position and the direction of the distal end portion 2*d* of the insertion section 2*b* change. Note that, in the 3D-model-image display section 32, the insertion section image 32*b* indicating a present visual line direction of the distal end portion 2*d* is displayed on the 3D model image 32*a*. Therefore, the examiner can easily understand where the examiner is currently observing.

When the distal end portion 2*d* is removed from the bladder B (S11: YES), the 2D-model-image display section 31 of the screen G1 displayed on the monitor 6 is in a state in which an image at a time when processing for a finally acquired endoscopic image is performed is displayed. On the 3D-model-image display section 32, only the 3D model image 32*a* in which the insertion section image 32*b* of the insertion section 2*b* is not displayed is displayed. A live image inside the bladder B is not displayed on the live-image display section 33.

The examiner may record an image of the 2D-model-image display section 31 in a nonvolatile memory section of the memory 22 as data of a clinical record of a patient. The examiner can print the image and paste the image onto the clinical record.

Conversion of a coordinate system and pasting of an endoscopic image are explained.

Figure 11:
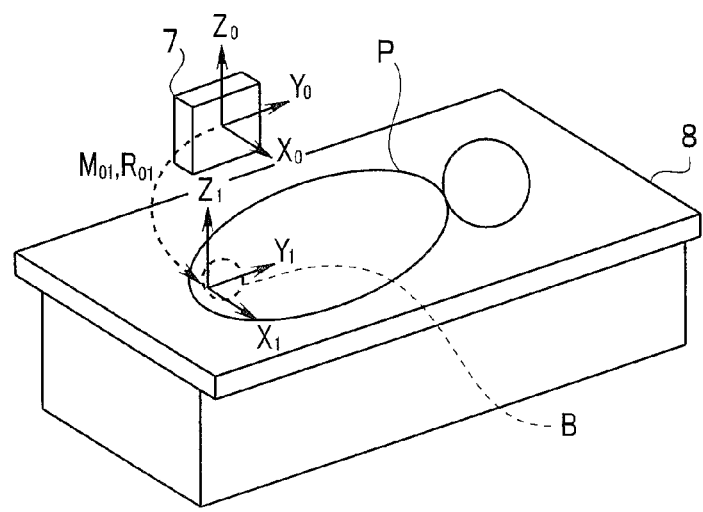
FIG. 11 is a diagram for explaining a relation between a coordinate system of a magnetic-field generating apparatus 7 and a coordinate system of the bladder B of a patent P on a bed 8 according to the first embodiment of the present invention.

FIG. 11 is a diagram for explaining a relation between a coordinate system of the magnetic-field generating apparatus 7 and a coordinate system of the bladder B of the patient P on the bed 8. The position/direction detecting section 25 generates, on a real-time basis, position/direction information based on the first coordinate system $(X_0Y_0Z_0)$ of the magnetic-field generating apparatus 7.

Therefore, in S3, as shown in FIG. 11, the CPU 21 determines a position and a direction of the entrance of the bladder B as a reference position and a reference direction and converts position/direction information of the position/direction detecting section 25 into position/direction information of the coordinate system $(X_1Y_1Z_1)$ based on the entrance of the bladder B according to the following Equation (1) and Equation (2).

$$P_1 = R_{01}P_0 + M_{01} \qquad \text{Equation (1)}$$

$$V_1 = R_{01}V_0 \qquad \text{Equation (2)}$$

$P_0$ and $V_0$ are respectively position and direction vectors in the first coordinate system $(X_0Y_0Z_0)$, which is a coordinate system based on the magnetic-field generating apparatus 7. $R_{01}$ is a rotation matrix indicated by the following Equation (3). $M_{01}$ is a translation matrix indicated by the following Equation (4).

$$R_{01} = \begin{pmatrix} r_{00} & r_{01} & r_{02} \\ r_{10} & r_{11} & r_{12} \\ r_{20} & r_{21} & r_{22} \end{pmatrix} \qquad \text{Equation (3)}$$

$$M_{01} = \begin{pmatrix} m_{x01} \\ m_{y01} \\ m_{z01} \end{pmatrix} \qquad \text{Equation (4)}$$

Therefore, a point $(x_0, y_0, z_0)$ on the first coordinate system $(X_0Y_0Z_0)$ is converted into a point $(x_1, y_1, z_1)$ on the intermediate coordinate system $(X_1Y_1Z_1)$ as indicated by the following Equation (5).

$$\begin{pmatrix} x_1 \\ y_1 \\ z_1 \end{pmatrix} = \begin{pmatrix} r_{00} & r_{01} & r_{02} \\ r_{10} & r_{11} & r_{12} \\ r_{20} & r_{21} & r_{22} \end{pmatrix} \begin{pmatrix} x_0 \\ y_0 \\ z_0 \end{pmatrix} + \begin{pmatrix} m_{x01} \\ m_{y01} \\ m_{z01} \end{pmatrix} \quad \text{Equation (5)}$$

When vectors in a position and a direction of the position/direction detecting section 25 at a time when the insertion of the distal end portion 2d of the endoscope into the bladder B is detected are represented as $P'_\theta$ and $V'_\theta$, the translation matrix $M_{01}$ is calculated by the following Equation (6).

$$M_{01} = P'_\theta \quad \text{Equation (6)}$$

Figure 12:
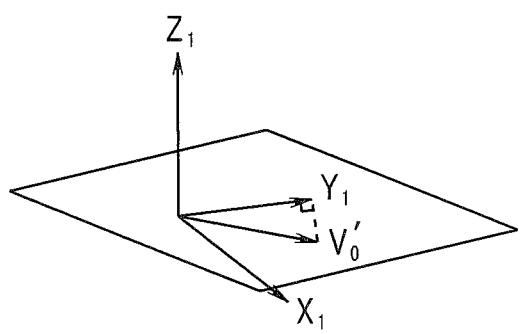
FIG. 12 is a diagram for explaining a direction vector projected on an intermediate coordinate system $(X_1Y_1Z_1)$ according to the first embodiment of the present invention.

The rotation matrix $R_{01}$ is calculated to satisfy conditions explained below. FIG. 12 is a diagram for explaining direction vectors projected on the intermediate coordinate system $(X_1Y_1Z_1)$. The conditions satisfied by the rotation matrix $R_{01}$ are that $Z_1$ is parallel to a gravity direction and $V'_\theta$ is projected on an $X_1Y_1$ plane perpendicular to $Z_1$, the projected vector direction is represented as $Y_1$, and a vector perpendicular to a $Y_1Z_1$ plane is represented as $X_1$.

Figure 13:
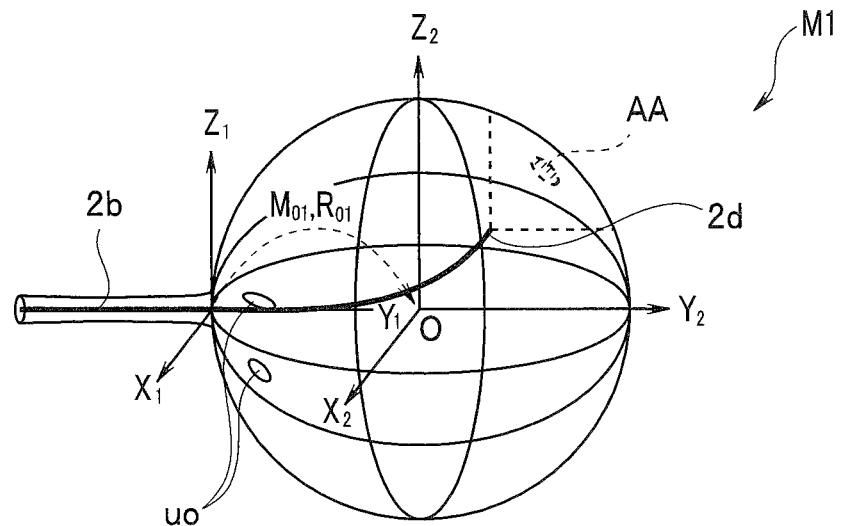
FIG. 13 is a diagram for explaining a relation between the intermediate coordinate system $(X_1Y_1Z_1)$ and a second coordinate system $(X_2Y_2Z_2)$ according to the first embodiment of the present invention.

In S6, further, the position and direction vectors of the intermediate coordinate system $(X_1Y_1Z_1)$ are converted into position and direction vectors in the second coordinate system $(X_2Y_2Z_2)$ based on a center of the 3D bladder model M1 according to the following Equation (7) and Equation (8). FIG. 13 is a diagram for explaining a relation between the intermediate coordinate system $(X_1Y_1Z_1)$ and the second coordinate system $(X_2Y_2Z_2)$.

$$P_2 = R_{12}P_1 + M_{O2} \quad \text{Equation (7)}$$

$$V_2 = R_{12}V_1 \quad \text{Equation (8)}$$

$P_1$ and $V_1$ are respectively position and direction vectors in the intermediate coordinate system $(X_1Y_1Z_1)$. $P_2$ and $V_2$ are respectively position and direction vectors in the second coordinate system $(X_2Y_2Z_2)$. $V_2$ is a direction vector of a pixel in a center of an endoscopic image in the second coordinate system $(X_2Y_2Z_2)$. $R_{12}$ is a rotation matrix indicated by the following Equation (9). $M_{O2}$ is a translation matrix indicated by the following Equation (10).

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} \quad \text{Equation (9)}$$

$$M_{O2} = \begin{pmatrix} m_{x12} \\ m_{y12} \\ m_{z12} \end{pmatrix} \quad \text{Equation (10)}$$

Therefore, the point $(x_1, y_1, z_1)$ on the intermediate coordinate system $(X_1Y_1Z_1)$ is converted into a point $(x_2, y_2, z_2)$ on the second coordinate system $(X_2Y_2Z_2)$ as indicated by the following Equation (11).

$$\begin{pmatrix} x_2 \\ y_2 \\ z_2 \end{pmatrix} = \begin{pmatrix} r'_{00} & r'_{01} & r'_{02} \\ r'_{10} & r'_{11} & r'_{12} \\ r'_{20} & r'_{21} & r'_{22} \end{pmatrix} \begin{pmatrix} x_1 \\ y_1 \\ z_1 \end{pmatrix} + \begin{pmatrix} m_{x12} \\ m_{y12} \\ m_{z12} \end{pmatrix} \quad \text{Equation (11)}$$

When the $X_1Y_1Z_1$ coordinate system is moved by $R_2$ in a $Y_1$ axis direction, translation $M_{12}$ and rotation $R_{12}$ are respectively as indicated by Equation (12) and Equation (13).

$$M_{12} = \begin{pmatrix} m_{x12} \\ m_{y12} \\ m_{z12} \end{pmatrix} = \begin{pmatrix} 0 \\ -R_2 \\ 0 \end{pmatrix} \quad \text{Equation (12)}$$

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} = \begin{pmatrix} 1 & 0 & 0 \\ 0 & 1 & 0 \\ 0 & 0 & 1 \end{pmatrix} \quad \text{Equation (13)}$$

As explained above, the position $P_0$ of the first coordinate system $(X_0Y_0Z_0)$ of the magnetic-field generating apparatus 7 is converted into the position $P_2$ of the second coordinate system $(X_2Y_2Z_2)$ based on the center of the 3D model according to Equation (5) and Equation (11). The direction $V_0$ in the first coordinate system $(X_0Y_0Z_0)$ is converted into the direction $V_2$ of the second coordinate system $(X_2Y_2Z_2)$ according to the following Equation (14).

$$V_2 = R_{12}R_{01}V_0 \quad \text{Equation (14)}$$

In the processing for pasting the endoscopic image in S7, calculation of a coordinate in pasting the endoscopic image onto an inner surface of the 3D bladder model M1 in the second coordinate system $(X_2Y_2Z_2)$ is explained.

Figure 14:
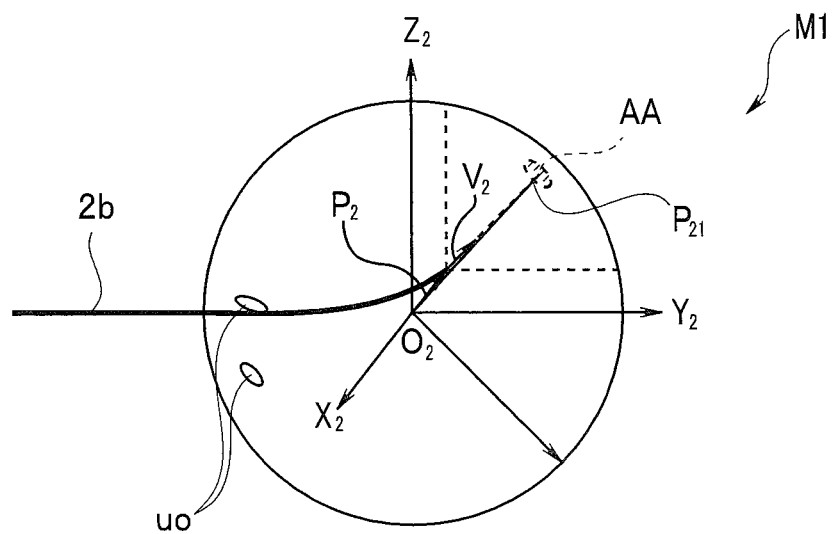
FIG. 14 is a diagram for explaining a coordinate on an inner surface of a sphere in the second coordinate system $(X_2Y_2Z_2)$ according to the first embodiment of the present invention.
Figure 15:
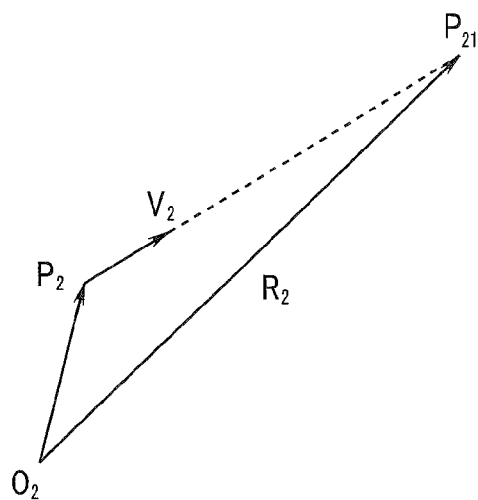
FIG. 15 is a diagram for explaining a position $P_2$ and a direction $V_2$ in the second coordinate system $(X_2Y_2Z_2)$ from a position and a direction vector of a distal end portion 2d according to the first embodiment of the present invention.

In the 3D model M1, a shape of the bladder B is assumed to be a sphere having a radius R2. The endoscopic image is pasted onto an inner surface of the sphere. FIG. 14 is a diagram for explaining a coordinate on an inner surface of a sphere in the second coordinate system $(X_2Y_2Z_2)$. FIG. 15 is a diagram for explaining the position $P_2$ and the direction $V_2$ in the second coordinate system $(X_2Y_2Z_2)$ from the position and direction vectors of the distal end portion 2d.

When the position $P_2$ and the direction $V_2$ in the second coordinate system $(X_2Y_2Z_2)$ of the distal end portion 2d are determined, a coordinate on the inner surface of the sphere of the obtained endoscopic image is calculated. To calculate the coordinate, a coefficient k satisfying the following Equation (15) and Equation (16) is calculated. A coordinate $P_{21}$ in the second coordinate system $(X_2Y_2Z_2)$ is calculated.

$$P_{21} = P_2 + kV_2 \quad \text{Equation (15)}$$

$$|P_{21}| = R_2 \quad \text{Equation (16)}$$

The endoscopic image is projected to a position of the calculated coordinate $P_{21}$ and pasted.

Subsequently, the position $P_{21}$ in the second coordinate system $(X_2Y_2Z_2)$ is projected on a coordinate system of a 2D model. First, in the case of a hemisphere on an abdomen side of the bladder B ($0 \leq Z_2$), left and right of a two-dimensional bladder model are reversed. Therefore, a value in a u direction is indicated by the following Equation (17) and a value in a v direction is indicated by the following Equation (18).

$$u = -x_{21} \quad \text{Equation (17)}$$

$$v = y_{21} + R_2 \quad \text{Equation (18)}$$

In the case of a hemisphere on a back side of the bladder B ($Z_2 < 0$), the left and right of the two-dimensional bladder model are reversed. Therefore, a value in the u direction is indicated by the following Equation (19) and a value in the v direction is indicated by the following Equation (20).

$$u = -x_{21} \quad \text{Equation (19)}$$

$$v = -y_{21} - R_2 \quad \text{Equation (20)}$$

Figure 16:
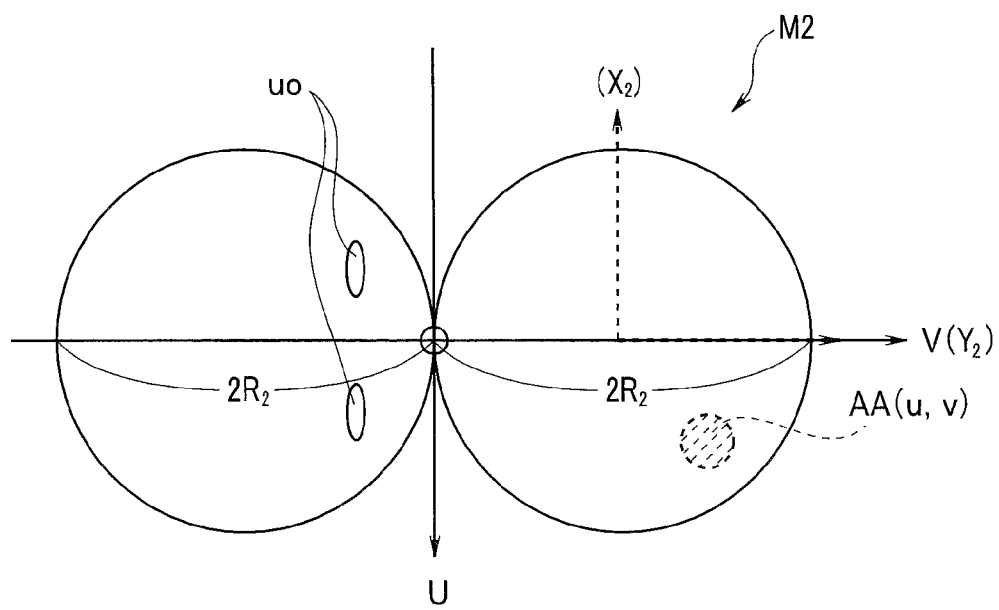
FIG. 16 is a diagram for explaining a coordinate relation in a two-dimensional coordinate system (U, V) according to the first embodiment of the present invention.

FIG. 16 is a diagram for explaining a coordinate relation in the two-dimensional coordinate system (U, V).

As explained above, the direction vector $V_2$ is the direction vector of the pixel in the image center of the endoscopic image in the second coordinate system $(X_2Y_2Z_2)$. Therefore, concerning pixels other than the pixel in the image center in the endoscopic image, it is possible to paste the entire endoscopic image onto the inner surface of the sphere of the second coordinate $(X_2Y_2Z_2)$ by calculating direction vectors of the pixels and repeating the conversion operation of Equation (15) to Equation (20) explained above.

Figure 17:
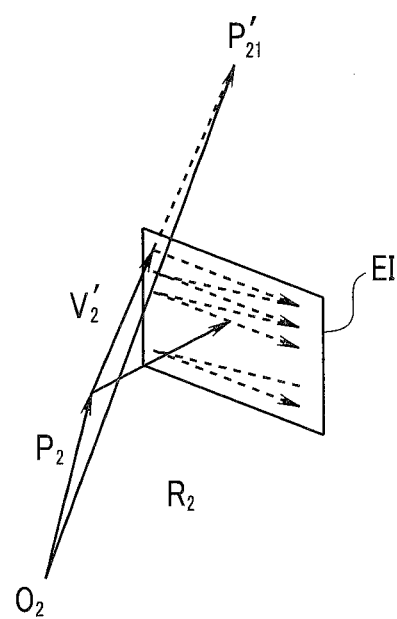
FIG. 17 is a diagram for explaining scanning of an entire endoscopic image and pasting of respective pixels onto an inner surface of a sphere of the second coordinate system $(X_2Y_2Z_2)$ according to the first embodiment of the present invention.

FIG. 17 is a diagram for explaining scanning of an entire endoscopic image and pasting of respective pixels to the inner surface of the sphere of the second coordinate system $(X_2Y_2Z_2)$. The pasting of the respective pixels onto the inner surface of the sphere of the second coordinate system $(X_2Y_2Z_2)$ is performed while respective pixels of an endoscopic image EI are scanned in a predetermined direction as indicated by a dotted line. In FIG. 17, $V_2'$ indicates a pasting vector of the respective pixels of the endoscopic image EI. $P_{21}'$ indicates a pasting vector to the inner surface of the sphere of the second coordinate system $(X_2Y_2Z_2)$.

As explained above, according to the present embodiment, the endoscopic image of the portion examined inside the bladder B is superimposed on the 2D model image 31a. The endoscopic image at the time when the release button 13 is pressed is superimposed and displayed on the forefront on the 2D model image 31a. Therefore, the examiner can easily check a region checked in the bladder B and clearly view an image of a lesion part or an interested part.

Note that, when the endoscopic image is pasted onto the 2D model image 31a, only the endoscopic image at the time when the release button 13 is pressed may be pasted.

Figure 18:
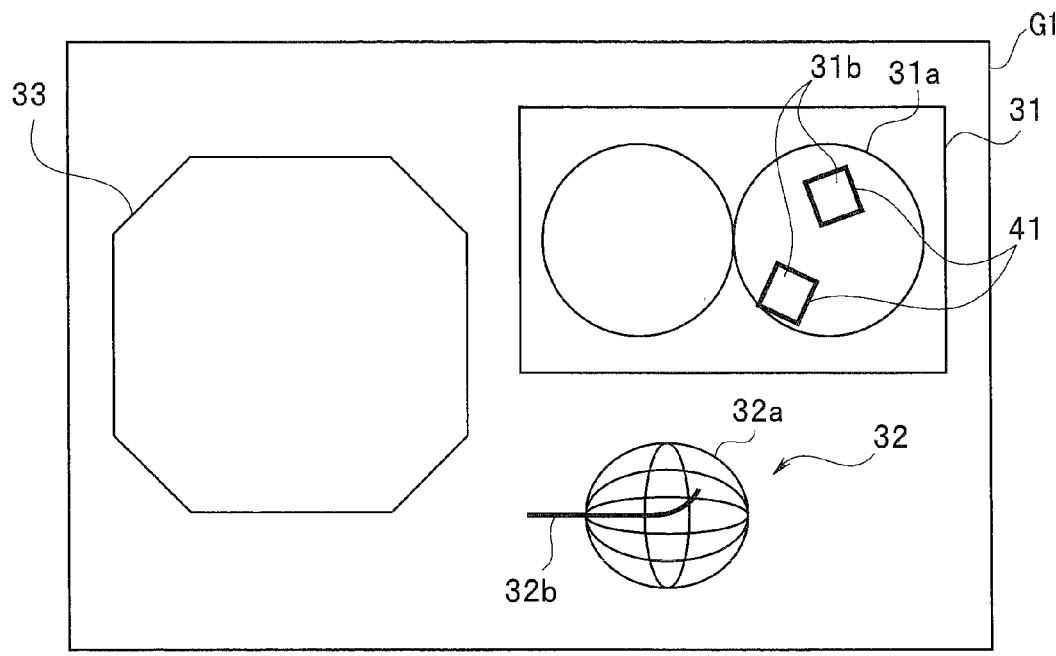
FIG. 18 is a diagram showing another example of the image displayed on the screen of the monitor 6 according to the first embodiment of the present invention.

FIG. 18 is a diagram showing another example of the image displayed on the screen of the monitor 6. In the 2D-model-image display section 31, only endoscopic images at a time when the release button 13 is pressed are pasted onto the 2D model image 31a. The predetermined frame images 41 are added to the endoscopic images at the time when the release button 13 is pressed. The examiner may also record an image of the 2D-model-image display section 31 shown in FIG. 18 in the nonvolatile memory section of the memory 22 as data of the clinical record of the patient. The examiner can print the image and paste the image onto the clinical record.

Further, a display state shown in FIG. 10 and a display state shown in FIG. 18 may be changed over.

In the example explained above, the magnetic sensor 12 is the six-axis sensor. Therefore, the plurality of endoscopic images pasted onto the 2D model image are pasted to be aligned in upward, downward, left, and right directions. However, the magnetic sensor 12 may be a five-axis sensor.

Figure 19:
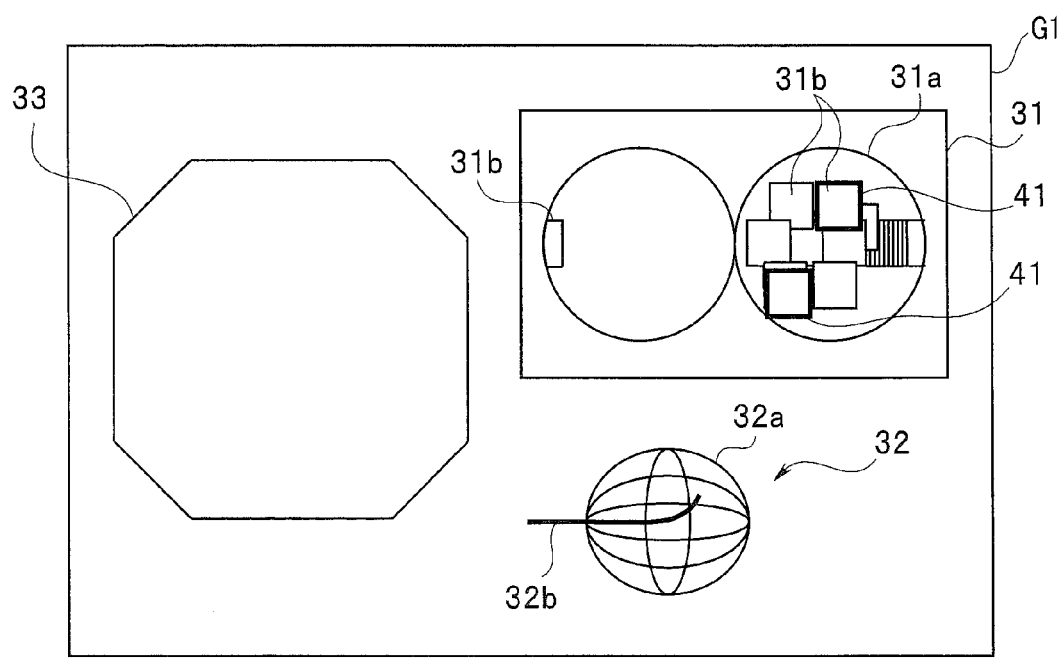
FIG. 19 is a diagram showing an example of an image displayed on the screen of the monitor 6 in a case in which a five-axis sensor is used according to the first embodiment of the present invention.
Figure 20:
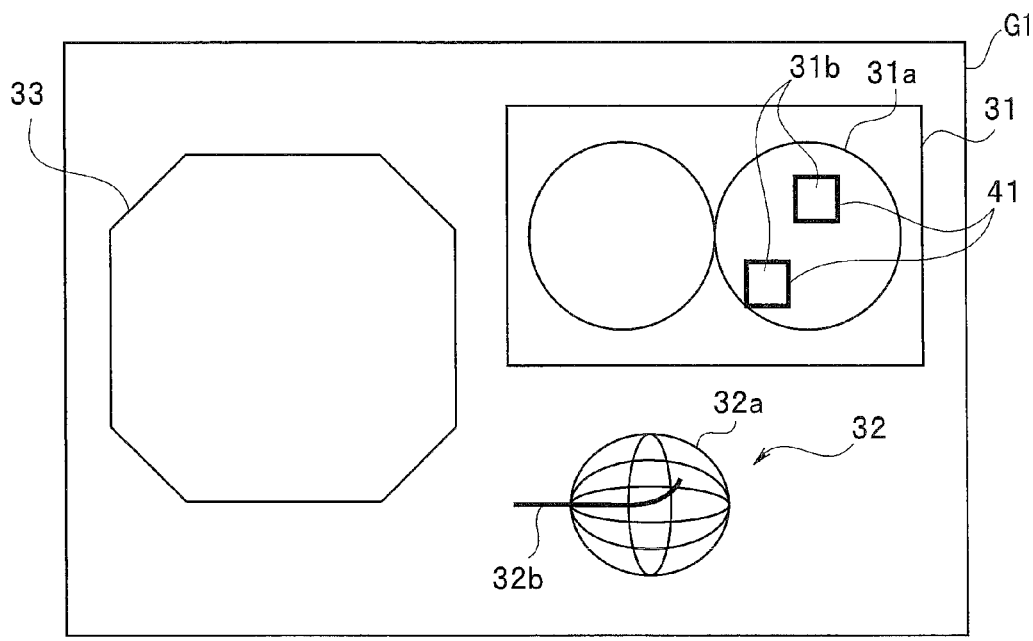
FIG. 20 is a diagram showing an example of an image in which only an endoscopic image at a time when a release button 13 is pressed is pasted onto a 2D model image 31a in the case in which the five-axis sensor is used according to the first embodiment of the present invention.

FIG. 19 is a diagram showing an example of an image displayed on the screen of the monitor 6 in a case in which the five-axis sensor is used. FIG. 20 is a diagram showing an example of an image in which only endoscopic images at a time when the release button 13 is pressed are pasted onto the 2D model image 31a in the case in which the five-axis sensor is used. FIG. 19 corresponds to FIG. 10. FIG. 20 corresponds to FIG. 18. In FIG. 19 and FIG. 20, the predetermined frame images 41 are added to the endoscopic images at the time when the release button 13 is pressed.

When the magnetic sensor 12 is the five-axis sensor, the magnetic sensor 12 cannot detect a turning angle around an axis of the insertion section 2b. However, as shown in FIG. 19 and FIG. 20, the respective endoscopic images 31b are pasted onto the 2D model image 31a at a predetermined angle unrelated to turning around the axis of the insertion section 2b.

When the five-axis sensor is used, effects same as the effects in the embodiment explained above can be obtained.

Furthermore, in the example explained above, the endoscopic image in the normal light observation mode is pasted onto the organ model image. However, the endoscopic image in the special light observation mode may be pasted onto the organ model image.

In this case, in FIG. 10 and FIG. 18 to FIG. 20 explained above, the endoscopic images 31b are endoscopic images of special light (narrowband light) rather than endoscopic images of normal light.

It is also possible that two organ model images are displayed, the endoscopic images of the normal light are pasted onto one of the organ model images, and the endoscopic images of the special light are pasted onto the other.

Figure 21:
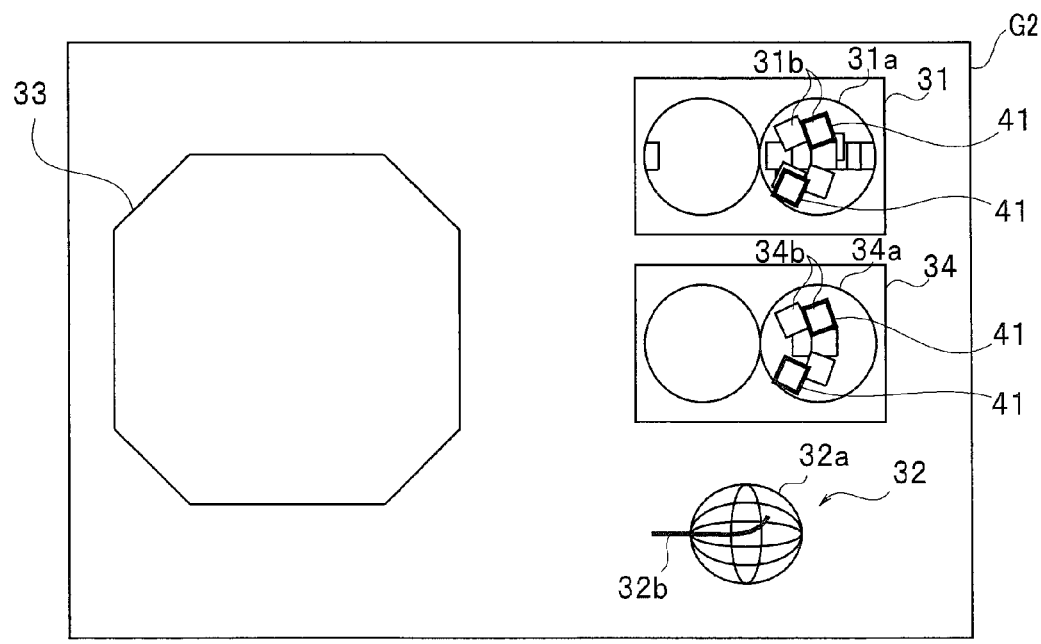
FIG. 21 is a diagram showing an example of a display screen on which images of two organ models are displayed to correspond to two observation modes according to the first embodiment of the present invention.

FIG. 21 is a diagram showing an example of a display screen in a case in which images of two organ models are displayed to correspond to the two observation modes.

In FIG. 21, components same the components in FIG. 10 and FIG. 18 to FIG. 20 are denoted by the same reference numerals and signs and explanation of the components is omitted. Note that FIG. 21 shows an example of a case in which the six-axis sensor is used.

In FIG. 21, in addition to the organ model image of the endoscopic images of the normal light, a 2D-model-image display section 34 for pasting the endoscopic images of the special light is added on the screen.

On the 2D-model-image display section 34, a 2D model image 34a and endoscopic images 34b of the special light pasted onto the 2D model image 34a by the processing in S7 and S9 are displayed. In FIG. 21 as well, the special frame images 41 are added to endoscopic images of the normal light and the special light at the time when the release button 13 is pressed.

The endoscopic images of the normal light are displayed on the 2D-model-image display section 31. The endoscopic images of the narrowband light are displayed on the 2D-model-image display section 34. Therefore, the examiner can perform an examination and the like while comparing both of the endoscopic images and, even after the examination, if both of the images are attached to a clinical record, the examiner can learn a state of an organ in a last examination more in detail.

Therefore, in S7 configuring the image generating section, a plurality of model images are set and endoscopic images corresponding to types of illumination light of the light source apparatus 4, which is the illuminating section, are pasted onto a plurality of models set on the basis of the types of the illumination light.

Note that the endoscopic images of the narrowband light indicate finer texture inside a mucous membrane surface compared with the endoscopic images of the normal light. The endoscopic images of the narrowband light at a time when the release button is pressed may be pasted onto a forefront on the 2D model image 31a of the 2D-model-image display section 31. An image on which both of the endoscopic images of the normal light and the endoscopic images of the narrowband light are pasted may be generated on one 2D-model-image display section.

Furthermore, the examiner viewing the endoscopic images can see according to a change of the endoscopic images displayed on the monitor 6 that the distal end portion 2*d* enters the bladder. Therefore, the examiner may record a reference position and a reference direction by performing predetermined operation in the operation section 2*a* or an operation panel of the processor 5 when the distal end portion 2*d* enters the bladder B. That is, alignment of the position and the direction of the objective optical window 11*a* and a coordinate system of the organ model image may be performed on the basis of a predetermined operation inputted by the examiner.

The examiner designates, outside a body cavity, a position where the endoscope enters the bladder from the urethra and sets a plane including the position (a plane perpendicular to a $Y_1$ direction of the coordinate system $(X_1 Y_1 Z_1)$ based on the entrance of the bladder B). A position and a direction at a time when the endoscope is inserted into the urethra and passes the plane may be recorded as a reference position and a reference direction. That is, alignment of the position and the direction of the objective optical window 11*a* and the coordinate system of the organ model image may be performed on the basis of position information with respect to a reference plane set in advance.

As explained above, with the endoscope system in the present embodiment explained above, it is possible to realize the endoscope system with which the examiner can easily see a position of an endoscopic image in an examination target organ and easily specify only specific endoscopic images for which the release button is pressed out of a plurality of endoscopic images.

Further, with the endoscope system in the present embodiment explained above, it is possible to easily check a position of a lesion part in the bladder B and a region being observed. Therefore, the lesion part is prevented from being overlooked. It is also possible to attain a reduction in a reexamination ratio and wrong description in a clinical record.

Next, modifications of a display method for making it easy to specify only specific endoscopic images for which the release button is pressed are explained.
(Modification 1)

In the embodiment explained above, by adding the frame images 41 to the endoscopic images to surround, with frames, the endoscopic images at the time when the release button is pressed among the plurality of endoscopic images, only the specific endoscopic images for which the release button is pressed are displayed distinguishably from the other endoscopic images. However, marks such as arrows pointing the endoscopic images at the time when the release button is pressed may be displayed.

Figure 22:
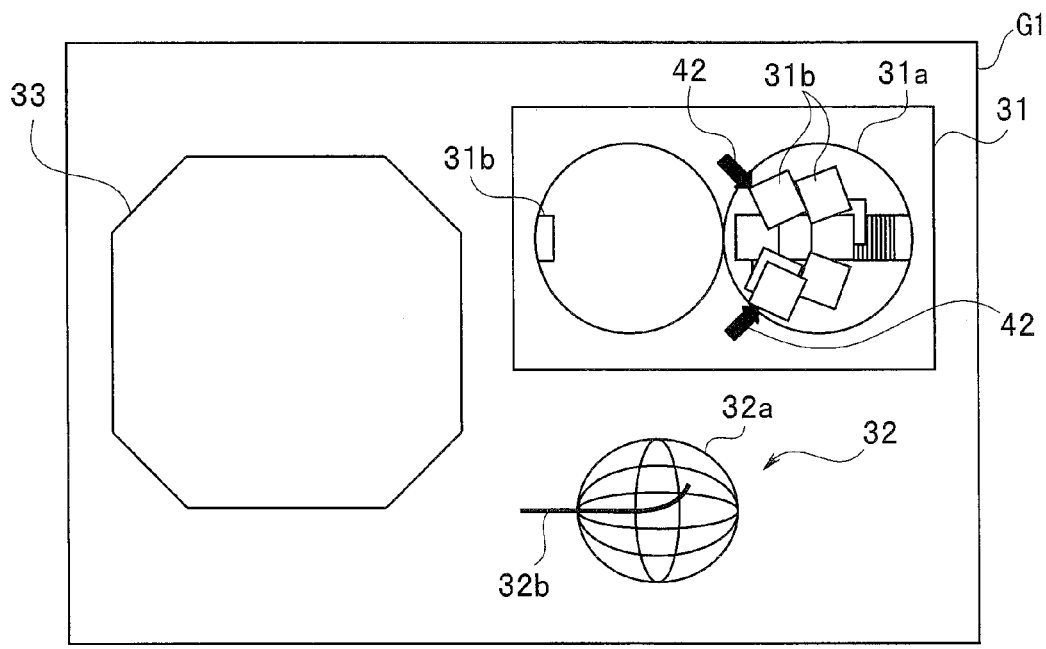
FIG. 22 is a diagram showing an example of a screen G1 on which only specific endoscopic images are displayed distinguishably from other endoscopic images according to modification 1 of the first embodiment of the present invention.

FIG. 22 is a diagram showing an example of the screen G1 on which only specific endoscopic images are displayed distinguishably from other endoscopic images according to modification 1.

As shown in FIG. 22, arrows 42 serving as marks pointing endoscopic images at a time when the release button is pressed are displayed together with the endoscopic images. The examiner can easily distinguish the endoscopic images pointed by the arrows 42. The predetermined processing in S9 is processing for adding predetermined marks (e.g., arrows) to intra-subject images at a time when a release signal, which is a predetermined trigger signal, is generated.

Therefore, the examiner can easily find the endoscopic images at the time when the release button is pressed.

(Modification 2)

In modification 1, the marks such as the arrows pointing the endoscopic images at the time when the release button is pressed are displayed. However, a tint of the endoscopic images at the time when the release button is pressed and a tint of the other endoscopic images may be differentiated.

Figure 23:
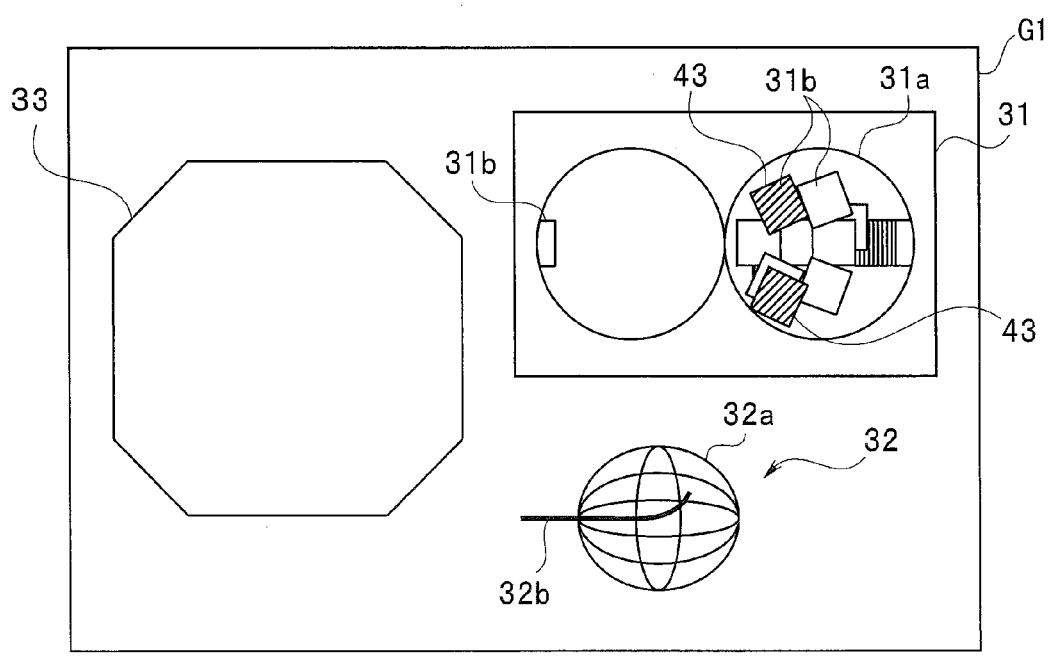
FIG. 23 is a diagram showing an example of the screen G1 on which only specific endoscopic images are displayed distinguishably from other endoscopic images according to modification 2 of the first embodiment of the present invention.

FIG. 23 is a diagram showing an example of the screen G1 on which only specific endoscopic images are displayed distinguishably from other endoscopic images according to modification 2.

As shown in FIG. 23, the plurality of endoscopic images 31*b* are displayed while differentiating a tint of endoscopic images 43 (indicated by hatching) at a time when the release button is pressed among the plurality of endoscopic images 31*b* and a tint of the other endoscopic images 31*b* for which the release button is not pressed. That is, the predetermined processing in S9 is processing for differentiating a color tone of intra-subject images at a time when a release signal, which is a predetermined trigger signal, is generated and a color tone of intra-subject images in a case in which the release signal, which is the predetermined trigger signal, is not generated in the determining section in S4.

As a method of differentiating the tints, for example, there is a method of displaying, in color, the endoscopic images 43 (indicated by the hatching) at the time when the release button is pressed and displaying, in monochrome, the other endoscopic images 31*b* for which the release button is not pressed to highlight the endoscopic images 43 (indicated by the hatching) at the time when the release button is pressed or displaying the endoscopic images 43 (indicated by the hatching) at the time when the release button is pressed with at least one of chroma and brightness set higher than at least one of chroma and brightness of the other endoscopic images 31*b* for which the release button is not pressed to increase contrast of the endoscopic images 43 (indicated by the hatching) at the time when the release button is pressed and highlight the endoscopic images 43. In both of the methods, the examiner can easily find, according to a difference of the tints, the endoscopic images at the time when the release button is pressed.
(Modification 3)

In modification 2 explained above, the tint of the endoscopic images at the time when the release button is pressed is differentiated from the tint of the other endoscopic images to make it possible to distinguish the endoscopic images. However, only the endoscopic images at the time when the release button is pressed may be displayed and the endoscopic images for which the release button is not pressed may be displayed in a color different from a color of a bladder development view (schema) in a background to clarify that the endoscopic images are already observed.

Figure 24:
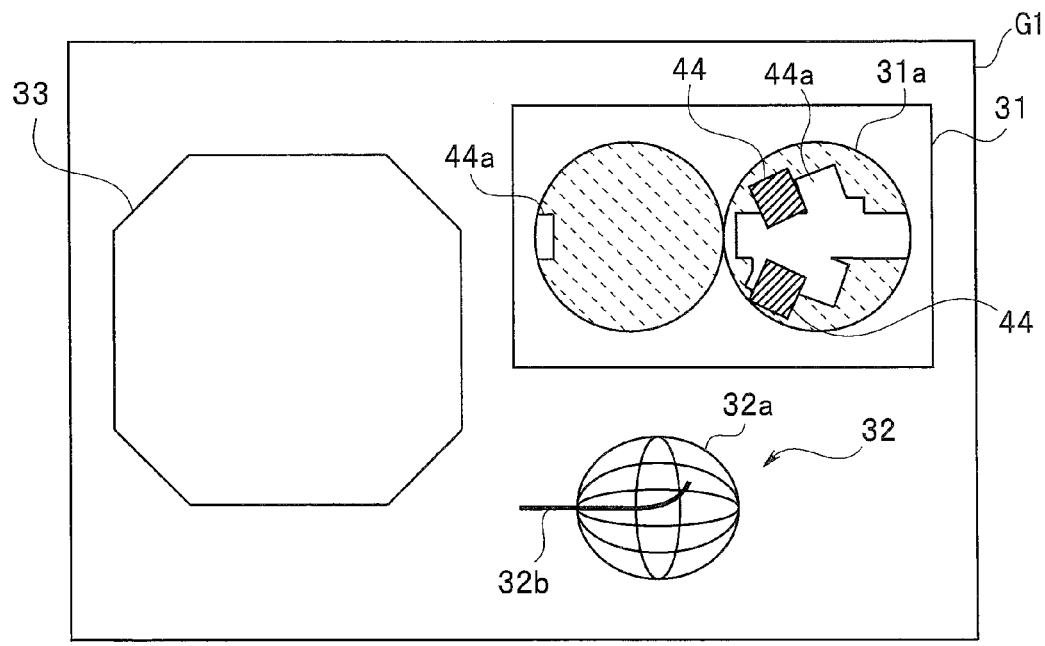
FIG. 24 is a diagram showing an example of the screen G1 on which only specific endoscopic images at a time when the release button is pressed are displayed distinguishably from other endoscopic images according to modification 3 of the first embodiment of the present invention.

FIG. 24 is a diagram showing an example of the screen G1 on which only specific endoscopic images at a time when the release button is pressed are displayed distinguishably from other endoscopic images according to modification 3.

As shown in FIG. 24, endoscopic images 44 (indicated by hatching) at a time when the release button is pressed among the plurality of picked-up endoscopic images 31*b* are displayed on a forefront and a region 44*a* of the other endoscopic images for which the release button is not pressed are painted out in a predetermined color different from a color (indicated by hatching of dotted lines) of a bladder development view (schema) in a background. That is, the predetermined processing in S9 is processing for differentiating a color tone of intra-subject images in a case in which a release signal, which is a predetermined trigger signal, is not generated from a color tone of a model image of a predetermined organ.

Therefore, the examiner can recognize an observed region at a glance with the region painted out in the predetermined color and can easily discriminate the endoscopic images at a time when the release button is pressed.

Figure 25:
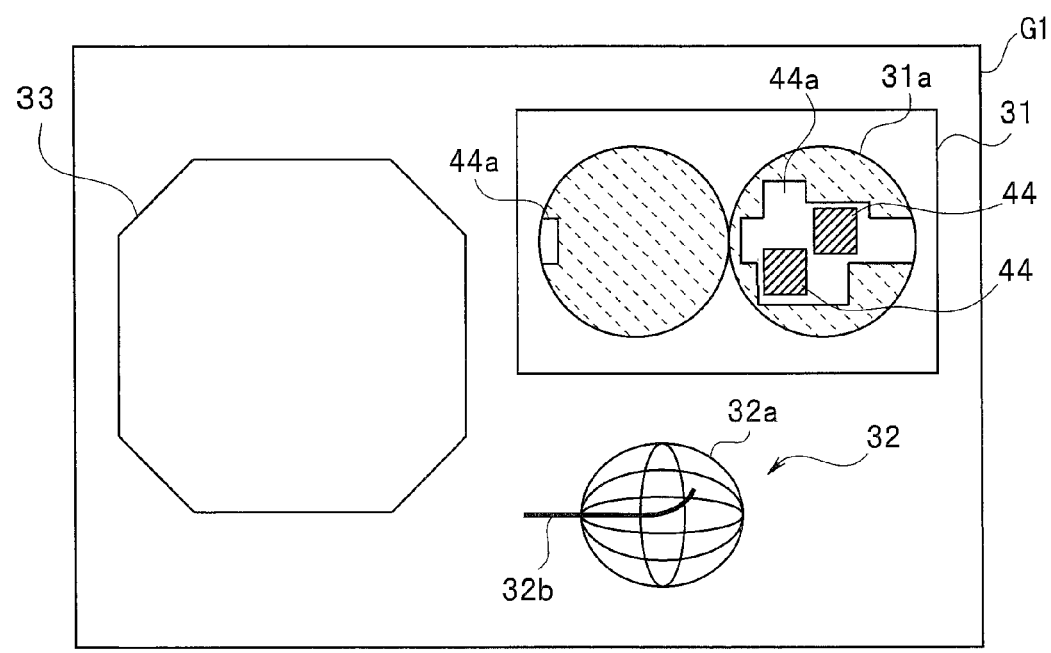
FIG. 25 is a diagram showing an example of the screen G1 in a case in which a magnetic sensor of a five-axis sensor is used according to modification 3 of the first embodiment of the present invention.

Note that FIG. 25 is a diagram showing an example of the screen G1 in a case in which a magnetic sensor of a five-axis sensor is used according to modification 3.

As explained above, according to the modifications explained above as well, it is possible to realize the endoscope system with which the examiner can easily see a position of an endoscopic image in an examination target organ and easily specify only specific endoscopic images for which the release button is pressed out of a plurality of endoscopic images.

Second Embodiment

The first embodiment is the endoscope system that makes it possible to easily specify only endoscopic images at the time when the release button is pressed. A second embodiment is an endoscope system that makes it possible to easily specify only endoscopic images at a time when a processing result of predetermined image processing or a determination result of presence or absence of a predetermined event is a predetermined result rather than specifying only the endoscopic images through the operation of the release button.

A configuration of the endoscope system in the second embodiment is the same as the configuration of the endoscope system in the first embodiment. Therefore, components same as the components in the first embodiment are denoted by the same reference numerals and signs and explanation of the components is omitted. Only different components are explained.

The endoscope system in the present embodiment includes the components shown in FIG. 1 and FIG. 2. Processing for pasting an endoscopic image onto an organ model image in the endoscope system in the present embodiment is different from the processing for pasting the endoscopic image onto the organ model image in the first embodiment.

Figure 26:
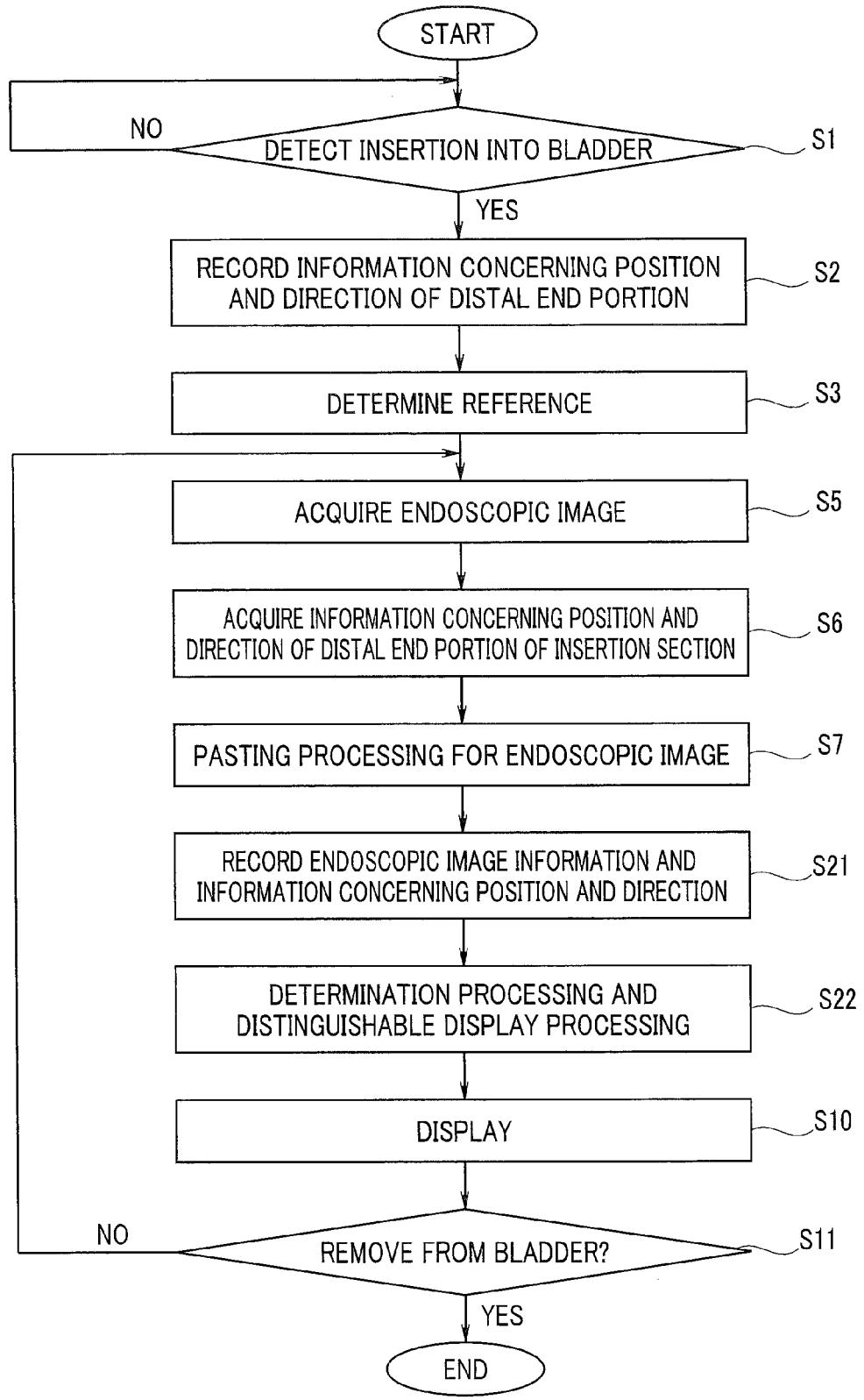
FIG. 26 is a flowchart for explaining an example of a flow of processing for pasting an endoscopic image onto a bladder model image during observation inside a bladder according to a second embodiment of the present invention.

FIG. 26 is a flowchart for explaining an example of a flow of processing for pasting an endoscopic image to a bladder model image during observation inside a bladder according to the present embodiment. In FIG. 26, processing same as the processing shown in FIG. 3 is denoted by the same reference signs and explanation of the processing is omitted.

In FIG. 26, after the reference determination (S3), the CPU 21 performs acquisition of an endoscopic image (S5). Thereafter, the CPU 21 executes acquisition of information concerning a position and a direction of the distal end portion 2d (S6) and processing for pasting the endoscopic image (S7).

Following S7, the CPU 21 performs processing for recording information concerning the endoscopic image and the information concerning the position and the direction (S21). After executing the processing in S21, the CPU 21 executes determination processing and distinguishable display processing (S22). The determination processing in S22 is determination processing for displaying an endoscopic image for which a predetermined determination result is obtained distinguishable from other endoscopic images.

Figure 27:
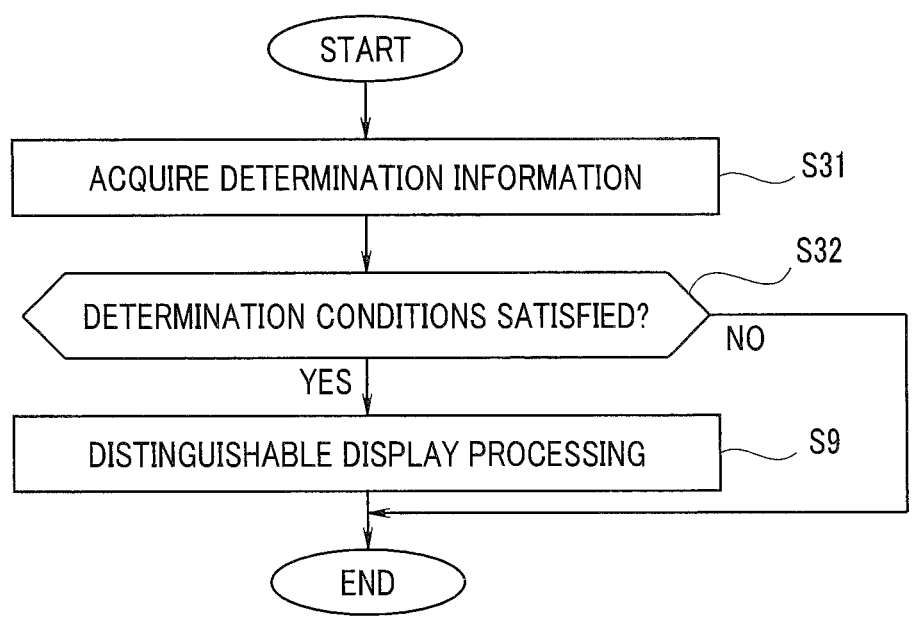
FIG. 27 is a flowchart for explaining an example of a flow of determination processing and distinguishable display processing according to the second embodiment of the present invention.

FIG. 27 is a flowchart for explaining an example of a flow of the determination processing and the distinguishable display processing. The CPU 21 acquires determination information (S31).

The determination information acquired in S31 is different depending on a determination method.

As the determination method, there are two methods, i.e., a method by image processing and a method by event detection. In the case of the method by image processing, as determination targets, there are a) presence or absence of an uneven portion having predetermined size (height) in an image, b) presence or absence of a portion in the image where a color tone is different from a color tone of a periphery, and c) presence or absence of a portion in the image where texture is different from texture of the periphery. In the case of the method by event detection, as determination targets, there are d) presence or absence of predetermined operation and e) presence or absence of mode changeover operation.

a) of the method by image processing is explained as an example.

In the case of a), the determination information acquired in S31 is information concerning size (i.e., height) of unevenness in an image.

The size of the unevenness in the image is calculated from position information of a predetermined plurality of points of two images, i.e., distance information from the image pickup device 11 to the respective points using a stereo measurement function. More specifically, concerning the predetermined plurality of points in the image, size (i.e., height) of unevenness of a part of a subject is calculated and obtained from a difference between a distance from the image pickup device 11 to one of adjacent two points and a distance from the image pickup device 11 to the other of the two points. For example, if a lesion part inside the bladder B swells and bulges, the bulging portion is a convex portion higher than a mucous membrane surface around the portion. Height of the convex portion on a subject surface in this intra-subject image configures a predetermined feature value.

Therefore, the CPU 21 acquires, as the determination information, a plurality of kinds of information concerning a difference between the adjacent two points obtained from a plurality of kinds of distance information from the image pickup device 11 to the predetermined plurality of points in the endoscopic image.

The CPU 21 determines, from the acquired determination information, whether a predetermined determination condition is satisfied (S32).

In the case of a), as the determination condition, it is determined whether a difference equal to or larger than a predetermined threshold (TH1) is present among the plurality of kinds of difference information. When a difference equal to or larger than the predetermined threshold (TH1) is present among the plurality of kinds of difference information, for example, a tumor is considered to be present. Therefore, it is determined that the predetermined determination condition is satisfied.

When a difference equal to or larger than the predetermined threshold (TH1) is present among the plurality of kinds of difference information (S32: YES), the CPU 21 executes the distinguishable display processing (S9). When a difference equal to or larger than the predetermined threshold (TH1) is absent among the plurality of kinds of difference information (S32: NO), the CPU 21 does not execute the processing in S9.

Thereafter, the CPU 21 executes display processing (S10) and repeats the processing in S5 to S10 until the insertion section 2b is removed from the bladder B.

Therefore, when it is determined by the image processing that a convex portion having predetermined size is present, the frame image 41 is automatically added to only an endoscopic image in which the convex portion is determined as being present. The endoscopic image is displayed distinguishably from the other endoscopic images. Therefore, the examiner can easily specify only the endoscopic image in which the convex portion is determined as being present.

The example explained above is the case of a). However, in the case of b) to e), determination information and a determination condition are different.

In the case of b), the determination information is a predetermined calculated value calculated from color information of respective pixels in an endoscopic image. The calculated value is, for example, an average value or a dispersion of pixel values calculated for each channel of RGB or a ratio of pixel values of RGB (e.g., G/R) calculated for each pixel. A color tone of this intra-subject image configures the predetermined feature value.

A determination condition is whether a difference between the predetermined calculated value obtained from the color information and a calculated value in another image or an image in the past is equal to or larger than a predetermined value. When the difference between the predetermined calculated value calculated from the endoscopic image and the calculated value in the other image or the like is equal to or larger than the predetermined value, it is determined that the determination condition is satisfied.

In the case of c), the determination information is texture information in the endoscopic image. The texture information is generated from information concerning a feature value (e.g., an edge element) extracted from the endoscopic image by the image processing. Texture of this intra-subject image configures the predetermined feature value. The determination condition is whether a difference between the obtained texture information and texture information in another image or an image in the past is equal to or larger than a predetermined value. For example, when the edge element is equal to or larger than an edge element in the other image or the image in the past, it is determined that the determination condition is satisfied.

In the case of d), the determination information is an amount of change of at least one kind of information of a position and a direction of the distal end portion 2d of the insertion section 2b. The information concerning the position and the direction of the distal end portion 2d is information obtained from the position/direction information of the magnetic sensor 12. The amount of change is information concerning a difference of at least one of the position and the direction.

For example, when the examiner performs, as a predetermined action, predetermined operation for quickly twisting the insertion section 2b around an axis (operation for, after twisting the insertion section 2b clockwise, quickly twisting the insertion section 2b in the opposite direction (counterclockwise), the direction of the distal end portion 2d greatly changes within a predetermined time. Therefore, the CPU 21 can calculate an amount of the change. An operation signal indicating the predetermined operation for the insertion section 2b of the endoscope provided with the image pickup device 11, which is an image pickup section, configures a predetermined trigger signal.

The determination condition is whether the amount of change is equal to or larger (or equal to or smaller) than a predetermined threshold. When the amount of change is equal to or larger (or equal to or smaller) than the predetermined value, it is determined that the determination condition is satisfied. When the determination condition is satisfied, endoscopic images to which the frame images 41 are automatically added are images stored in the memory 22 immediately before it is determined that the predetermined condition is satisfied. That is, since a plurality of endoscopic images captured by the image capturing section 24 are stored in the memory 22, endoscopic images earlier by a predetermined time or by a predetermined number of frames than time of the determination that the predetermined condition is satisfied are selected and the frame images 41 are added to the endoscopic images.

Note that the amount of change may be an amount of change indicating a stationary state without changes in a position and a direction for a predetermined time.

In the case of e), the determination information is information concerning an operation signal of the changeover switch 5a. The operation signal of the changeover switch 5a is supplied from the processor 5 to the CPU 21 via the image capturing section 24. Such a changeover signal for the observation mode in picking up an image of an inside of a subject configures the predetermined trigger signal.

The determination condition is whether there is a change of the observation mode on the basis of an operation signal. When there is a change in the observation mode, it is determined that the determination condition is satisfied.

The endoscope system 1 has two modes, i.e., a normal light observation mode and a special light observation mode. However, the endoscope system 1 may have a PDD mode and the like for a photodynamic diagnostic method (PDD).

Therefore, the processing in S7 and S22 configures a display section that applies, to the intra-subject image, when it is determined in the determining section in S32 that the predetermined trigger signal is generated or the predetermined feature value satisfies the predetermined condition, the predetermined processing in S9 for distinguishably displaying an intra-subject image at a time when the predetermined trigger signal is generated or a predetermined feature value satisfies the predetermined condition and displays an image obtained by pasting the intra-subject image onto the model image of the predetermined organ associated by the associating section in S6.

As explained above, when the method by image processing of b) and c) and the method by event detection of d) and e) are used, as in the case of a), the frame images 41 are automatically added to only desired endoscopic images. It is possible to distinguishably display only specific endoscopic images.

That is, the processing in S32 configures a determining section that determines whether an operation signal (a signal for predetermined twisting operation or a mode changeover signal) serving as the predetermined trigger signal concerning the image pickup in the image pickup device 11 is generated or whether a predetermined feature value (unevenness, a color tone, or texture) in the intra-subject image satisfies a predetermined condition.

Note that, rather than using any one determination method among a) to e), two or more of a) to e) explained above may be combined as a determination condition.

Note that the three modifications explained in the first embodiment are applicable in the second embodiment as well.

That is, the predetermined processing in S9 may be processing for, as in modification 1, adding predetermined marks to intra-subject images at a time when the predetermined trigger signal is generated or the predetermined feature value satisfies the predetermined condition, as in modification 2, differentiating a color tone of an intra-subject image at a time when the predetermined trigger signal is generated or the predetermined feature value satisfies the predetermined condition and a color tone of an intra-subject image in the case in which the predetermined trigger signal is not generated or the predetermined feature value does not satisfies the predetermined condition in the determining section in S32, or, as in modification 3, differentiating a color tone of an intra-subject image in the case in which the predetermined trigger signal is not generated or in the case in which the predetermined feature value does not satisfy the predetermined condition in the determining section in S32 and a color tone of a model image of a predetermined organ.

As explained above, according to the respective embodiments explained above, the endoscopic image is pasted onto the organ model image of the target organ to allow the examiner to easily see a position of the endoscopic image in the examination target organ and easily specify only specific endoscopic images out of a plurality of endoscopic images. Therefore, it is possible to realize the endoscope system that can reduce an examination time or a treatment time by the endoscope.

Note that, in the respective embodiments explained above, specific endoscopic images are distinguishably displayed by adding the frame images to the endoscopic images pasted onto the organ model image. However, in addition to distinguishably displaying the endoscopic images, enlarged images of the specific endoscopic images may be displayed together.

Figure 28:
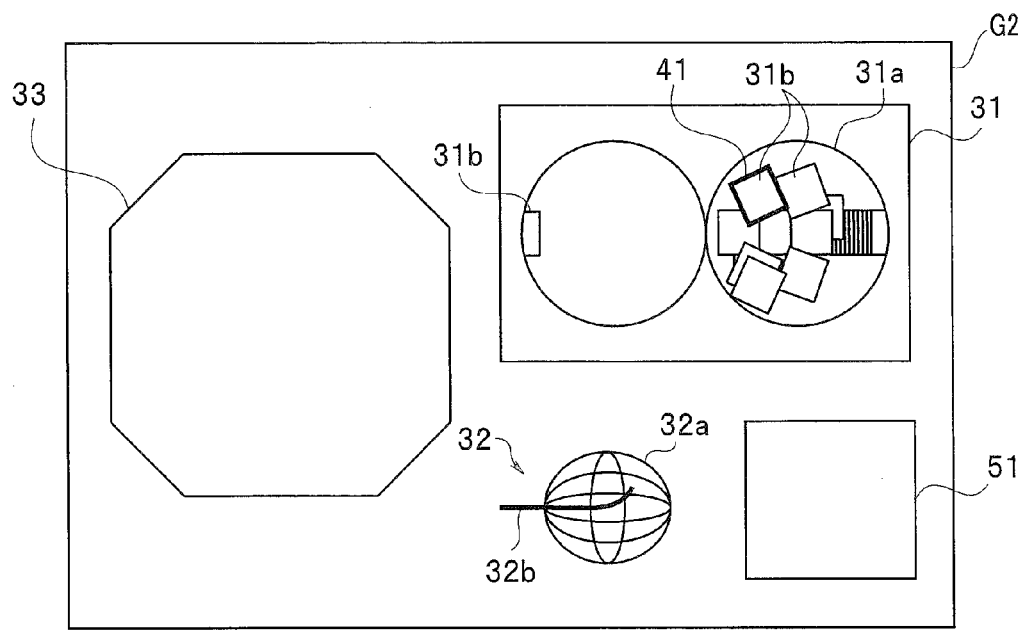
FIG. 28 is a diagram showing an example of a screen on which an enlarged image is displayed together with an organ model image on a display screen displayed on the screen of the monitor 6.
Figure 29:
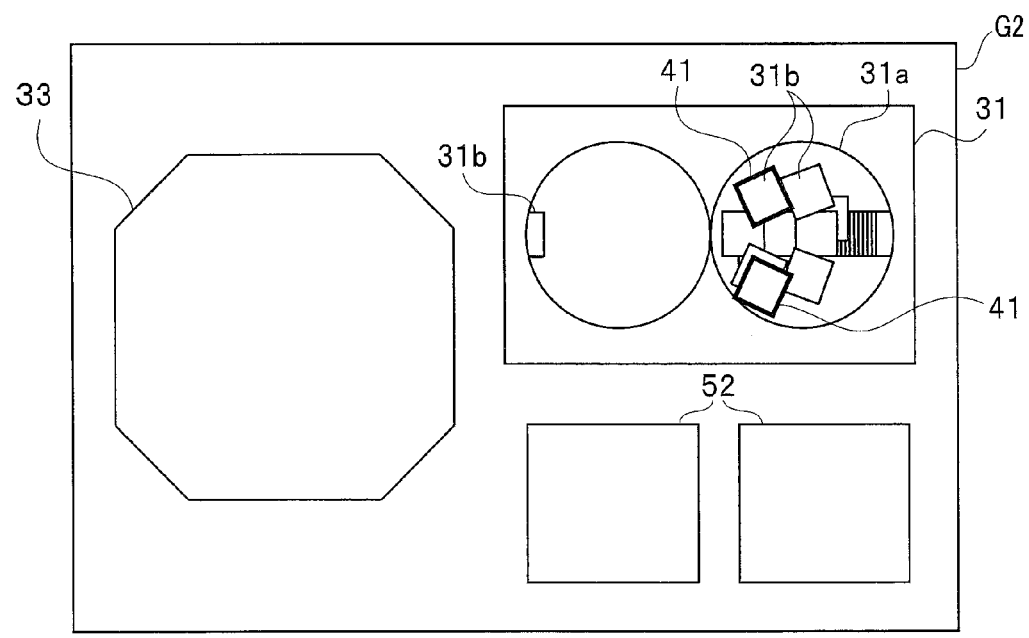
FIG. 29 is a diagram showing an example of a screen on which an enlarged image is displayed together with an organ model image on the display screen displayed on the screen of the monitor 6.
Figure 30:
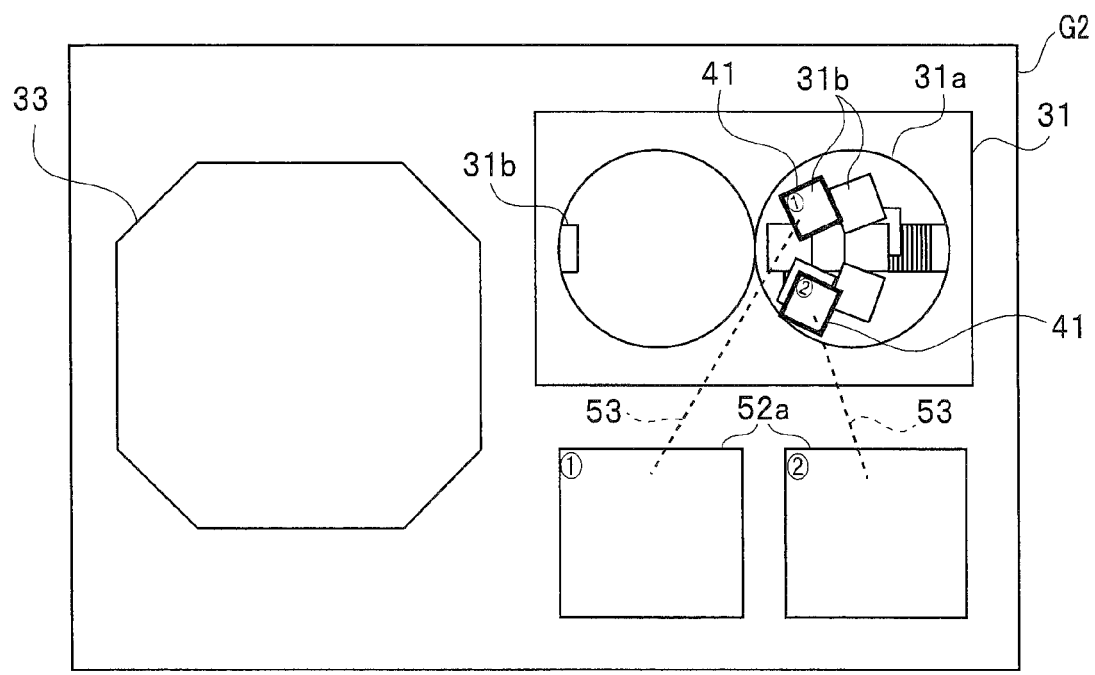
FIG. 30 is a diagram showing an example of a screen on which an enlarged image is displayed together with an organ model image on the display screen displayed on the screen of the monitor 6.

FIG. 28 to FIG. 30 are diagrams showing examples of a screen on which an enlarged image is displayed together with an organ model image on the display screen displayed on the screen of the monitor 6.

In FIG. 28, for example, the frame image 41 is added to the endoscopic image 31b at a time when the release button is pressed. An enlarged display section 51 that displays an enlarged image of the endoscopic image 31b added with the frame image 41 is displayed on a screen G2. By viewing an endoscopic image displayed on the enlarged display section 51, the examiner can easily check the endoscopic image at a time when the release button is pressed, for example, check whether an image of a lesion part is appropriately picked up.

In FIG. 29, for example, the frame images 41 are added to the endoscopic images 31b at a time when the release button is pressed a plurality of times (in FIG. 29, twice). Enlarged display sections 52 that display enlarged images of two endoscopic images 31b added with the frame images 41 are displayed on the screen G2.

In FIG. 30, for example, the frame images 41 are added to the endoscopic images 31b at a time when the release button is pressed a plurality of times (in FIG. 30, twice). Enlarged display sections 52a that display, together with correspondence numbers of endoscopic images added with the frame images 41, enlarged images of two endoscopic images 31b added with the frame images 41 are displayed on the screen G2. As shown in FIG. 30, encircled numbers for identification are added to the two endoscopic images. The encircled numbers for identification are also added to the enlarged images of the enlarged display sections 52a.

Note that, in FIG. 29 and FIG. 30, since a plurality of enlarged images are displayed, the 3D-model-image display section 32 is not displayed.

Therefore, the examiner can easily grasp to which of the endoscopic images added with the frame images displayed on the 2D-model-image display section 31 the respective endoscopic images enlarged and displayed on the enlarged display section 52a correspond. In FIG. 30, correspondence relations between the endoscopic images on the bladder development view (schema) and the enlarged images are indicated by the numbers. However, characters, signs, or the like may be used instead of the numbers. Further, the correspondence relations between the endoscopic images on the bladder development view (schema) and the enlarged images may be indicated by lines that connect the endoscopic images and the enlarged images, as indicated by dotted lines 53 in FIG. 30.

Note that, in FIG. 28 to FIG. 30, all the enlarged images are always displayed during an examination. However, all the enlarged images may be displayed at any timing designated by the examiner, for example, only when the examiner presses a predetermined button.

Alternatively, for example, when the frame images 41 are added to a plurality of endoscopic images, when the examiner moves a pointer on the screen to an endoscopic image, an enlarged image of only the endoscopic image pointed by the pointer may be displayed.

As explained above, such an enlarged display section may be provided in the respective embodiments and the respective modifications explained above.

In the respective embodiments explained above, the endoscopic image is pasted onto the two-dimensional organ model image. However, the endoscopic image may be pasted onto an image of a three-dimensional organ model, which is a 3D image. That is, the model image may be a 3D image rather than the 2D image.

Furthermore, in the respective embodiments explained above, the endoscopic image inside the bladder is pasted onto the 2D model image of the bladder. However, the endoscope system in the respective embodiments explained above is also applicable to organs other than the bladder, for example, a stomach and a womb.

Reference information can be determined from a change of an image and can be pasted onto the organ model image, for example, in the case of the stomach, when the endoscope enters the stomach from an esophagus, in the case of a lung, when the endoscope enters left or right bronchus first in a lower part of the trachea, and, in the case of the womb, when the endoscope enters inside the womb from a uterine cervix.

In the two embodiments explained above, the endoscope 2 is a flexible endoscope including an insertion section having flexibility. However, the present invention is also applicable to other types of endoscopes such as a rigid endoscope and a scanning-type endoscope. Further, the present invention is also applicable to an endoscope in which an insertion section includes a light guide member that guides light made incident on an objective optical window at a distal end portion to a proximal end portion.

Further, the endoscope system explained above is used to record or display a position of an endoscopic image inside an organ. However, the endoscope system can also be used for recording of a biopsy position in a random biopsy.

The present invention is not limited to the embodiments explained above. Various changes, alterations, and the like are possible in a range in which the gist of the present invention is not changed.

What is claimed is:
1. An endoscope system comprising:
   an insertion section configured to be inserted into a subject;

an objective optical window provided on a distal end side of the insertion section and configured to receive light from the subject;
an image pickup sensor configured to pick up an image inside the subject from the light made incident from the objective optical window;
a position-information acquiring sensor configured to acquire position information of the objective optical window; and
a central processing unit configured to:
control a memory to record an intra-subject image picked up by the image pickup sensor and the position information acquired by the position-information acquiring sensor in association with each other;
associate the position information recorded in the memory with a model image of a predetermined organ in the subject;
generate, as a pasted image, an image obtained by pasting the intra-subject image onto the model image of the predetermined organ;
determine whether a predetermined trigger signal concerning the image pickup in the image pickup sensor is generated or a predetermined feature value of the intra-subject image picked up by the image pickup sensor satisfies a predetermined condition; and
apply processing for pasting the intra-subject image, concerning which the predetermined trigger signal is determined as being generated or the predetermined feature value of which is determined as satisfying the predetermined condition, onto a forefront on the pasted image relative to other intra-subject images and apply image processing to the intra-subject image pasted onto the forefront to be distinguishable from the other intra-subject images.

2. The endoscope system according to claim 1, wherein the predetermined trigger signal is a release signal for recording the intra-subject image acquired by the image pickup sensor, an operation signal indicating predetermined operation for the insertion section of an endoscope in which the image pickup sensor is provided, or a changeover signal for an observation mode in picking up an image inside the subject.

3. The endoscope system according to claim 1, wherein the predetermined feature value is height of a convex portion on a subject surface in the intra-subject image, a color tone of the intra-subject image, or texture of the intra-subject image.

4. The endoscope system according to claim 1, wherein, when it is determined that the predetermined trigger signal is not generated or the predetermined feature value does not satisfy the predetermined condition, the central processing unit is configured to not perform the image processing for making the intra-subject image to be distinguishable from the other intra-subject images on the intra-subject image pasted image.

5. The endoscope system according to claim 1, wherein the central processing unit is configured to add a frame image to the intra-subject image pasted onto the forefront.

6. The endoscope system according to claim 1, wherein the central processing unit is configured to add a predetermined mark to the intra-subject image pasted onto the forefront.

7. The endoscope system according to claim 1, wherein the central processing unit is configured to differentiate a color tone of the intra-subject image pasted onto the forefront and a color tone of the other intra-subject images.

8. The endoscope system according to claim 1, wherein the central processing unit is configured to paint out the other intra-subject images in a predetermined color.

9. The endoscope system according to claim 1, wherein the central processing unit is configured to:
apply spectral estimation processing to the intra-subject image; and
apply the predetermined processing to a plurality of models set according to operation modes and perform pasting of the intra-subject image.

10. The endoscope system according to claim 1, wherein the central processing unit is configured to generate an enlarged image of the intra-subject image to which the image processing is applied.

11. The endoscope system according to claim 1, wherein the intra-subject image is an image inside a bladder of the subject, and
wherein the model image is a model image of the bladder.

12. The endoscope system according to claim 11, wherein the model image is a 2D bladder development view.

13. The endoscope system according to claim 1, further comprising an instruction input device configured to receive the predetermined trigger signal inputted by an operator,
wherein when the predetermined trigger signal is inputted, the central processing unit is configured to apply the image processing for distinguishing the intra-subject image picked up by the image pickup sensor from other intra-subject images on the intra-subject image pasted image.

14. The endoscope system according to claim 1, wherein, when a plurality of intra-subject images, concerning which the predetermined trigger signal is determined as being generated or the predetermined feature value of which is determined as satisfying the predetermined condition, are superimposed, the central processing unit is configured to paste an intra-subject image to which the image processing is applied later in time series onto an intra-subject image to which the image processing is applied earlier in time series.

15. The endoscope system according to claim 1, wherein, when a plurality of intra-subject images, concerning which the predetermined trigger signal is determined as being generated or the predetermined feature value of which is determined as satisfying the predetermined condition, are superimposed, the central processing unit is configured to apply the image processing to make the plurality of intra-subject images distinguishable from one another.

16. An actuation method for an endoscope system comprising:
an image pickup sensor configured to pick up an image inside a subject from light made incident from an objective optical window provided on a distal end side of an insertion section configured to be inserted into the subject;
a position-information acquiring sensor configured to acquire position information of the objective optical window; and
a memory configured to record an intra-subject image acquired by the image pickup sensor and the position information acquired by the position-information acquiring sensor in association with each other, wherein the actuation method comprises:

associating the position information recorded in the memory with a model image of a predetermined organ in the subject;

generating, as an intra-subject image pasted image, an image obtained by pasting the intra-subject image onto the model image of the predetermined organ;

determining whether a predetermined trigger signal concerning the image pickup in the image pickup sensor is generated or a predetermined feature value of the intra-subject image acquired by the image pickup sensor satisfies a predetermined condition; and applying processing for pasting the intra-subject image, concerning which the predetermined trigger signal is determined as being generated or the predetermined feature value of which is determined as satisfying the predetermined condition, onto a forefront on the pasted image relative to other intra-subject images and applying image processing to the intra-subject image pasted onto the forefront to be distinguishable from the other intra-subject images.

17. The actuation method for the endoscope system according to claim 16, wherein the predetermined trigger signal is a release signal for recording the intra-subject image acquired by the image pickup sensor, an operation signal indicating predetermined operation for the insertion section of an endoscope in which the image pickup sensor is provided, or a changeover signal for an observation mode in picking up an image inside the subject.

* * * * *